(12) United States Patent
Golda et al.

(10) Patent No.: US 11,786,182 B2
(45) Date of Patent: Oct. 17, 2023

(54) HEALTH MONITORING SYSTEMS AND METHODS

(71) Applicant: RDS, Strasbourg (FR)

(72) Inventors: George Stefan Golda, El Granada, CA (US); Daniel Van Zandt Moyer, Menlo Park, CA (US); Mark P. Marriott, Palo Alto, CA (US); Sam Eletr, Paris (FR); Bruce O'Neil, Greenbrae, CA (US)

( * ) Notice: Subject to any disclaimer, the term of this patent is extended or adjusted under 35 U.S.C. 154(b) by 144 days.

(21) Appl. No.: 17/216,348

(22) Filed: Mar. 29, 2021

(65) Prior Publication Data

US 2021/0212638 A1 Jul. 15, 2021

Related U.S. Application Data

(63) Continuation of application No. 15/728,215, filed on Oct. 9, 2017, now Pat. No. 10,959,678, which is a (Continued)

(51) Int. Cl.
*A61B 5/00* (2006.01)
*A61B 5/259* (2021.01)
(Continued)

(52) U.S. Cl.
CPC .......... *A61B 5/7214* (2013.01); *A61B 5/0002* (2013.01); *A61B 5/0059* (2013.01); *A61B 5/0205* (2013.01); *A61B 5/0261* (2013.01); *A61B 5/0295* (2013.01); *A61B 5/02125* (2013.01); *A61B 5/02141* (2013.01); *A61B 5/08* (2013.01); *A61B 5/11* (2013.01); *A61B 5/259* (2021.01); *A61B 5/282* (2021.01); *A61B 5/318* (2021.01); *A61B 5/335* (2021.01); *A61B 5/6828* (2013.01); *A61B 5/72* (2013.01); *A61B 5/7207* (2013.01); *A61B 5/0006* (2013.01); (Continued)

(58) Field of Classification Search
None
See application file for complete search history.

(56) References Cited

U.S. PATENT DOCUMENTS 3,769,669 A 11/1973 Peacock et al.
3,830,970 A 8/1974 Hurley et al.
(Continued)

FOREIGN PATENT DOCUMENTS

CN 2785556 Y 6/2006
CN 101822533 A 9/2010
(Continued)

OTHER PUBLICATIONS

Extended European Search Report for Application No. EP19194996 issued by the European Patent Office, dated Apr. 22, 2020, 18 pages, EPO, Munich, Germany.
(Continued)

*Primary Examiner* — Shirley X Jian
(74) *Attorney, Agent, or Firm* — EIP US LLP; Jared A. Barnard

(57) ABSTRACT

Systems, methods and devices for reducing noise in health monitoring including monitoring systems, methods and/or devices receiving a health signal and/or having at least one electrode or sensor for health monitoring.

17 Claims, 22 Drawing Sheets

Related U.S. Application Data continuation of application No. 14/565,412, filed on Dec. 9, 2014, now Pat. No. 9,782,132, which is a continuation-in-part of application No. PCT/US2013/063748, filed on Oct. 7, 2013, which is a continuation of application No. 13/837,748, filed on Mar. 15, 2013, now Pat. No. 10,413,251, said application No. 14/565,412 is a continuation-in-part of application No. 13/837,748, filed on Mar. 15, 2013, now Pat. No. 10,413,251.

(60) Provisional application No. 62/038,768, filed on Aug. 18, 2014, provisional application No. 62/008,959, filed on Jun. 6, 2014, provisional application No. 62/000,975, filed on May 20, 2014, provisional application No. 61/932,100, filed on Jan. 27, 2014, provisional application No. 61/932,094, filed on Jan. 27, 2014, provisional application No. 61/710,768, filed on Oct. 7, 2012.

(51) Int. Cl.

| | | |
|---|---|---|
| *A61B 5/282* | (2021.01) | |
| *A61B 5/318* | (2021.01) | |
| *A61B 5/335* | (2021.01) | |
| *A61B 5/0205* | (2006.01) | |
| *A61B 5/026* | (2006.01) | |
| *A61B 5/0295* | (2006.01) | |
| *A61B 5/11* | (2006.01) | |
| *A61B 5/08* | (2006.01) | |
| *A61B 5/021* | (2006.01) | |
| *A61B 5/024* | (2006.01) | |
| *A61B 5/352* | (2021.01) | |
| *A61B 5/1455* | (2006.01) | |

(52) U.S. Cl.
CPC ......... *A61B 5/02438* (2013.01); *A61B 5/1118* (2013.01); *A61B 5/14551* (2013.01); *A61B 5/14552* (2013.01); *A61B 5/352* (2021.01); *A61B 5/6833* (2013.01); *A61B 5/721* (2013.01); *A61B 5/7275* (2013.01); *A61B 2560/0295* (2013.01); *A61B 2560/0412* (2013.01)

(56) References Cited

U.S. PATENT DOCUMENTS

| | | | |
|---|---|---|---|
| 3,911,906 A | 10/1975 | Reinhold, Jr. | |
| 4,141,366 A | 2/1979 | Cross, Jr. et al. | |
| 4,164,215 A | 8/1979 | Finlayson et al. | |
| 4,221,223 A | 9/1980 | Linden | |
| 4,224,948 A | 9/1980 | Cramer | |
| 4,230,127 A | 10/1980 | Larson | |
| 4,295,472 A | 10/1981 | Adams | |
| 4,360,030 A | 11/1982 | Citron et al. | |
| 4,412,546 A | 11/1983 | Barthels | |
| 4,494,550 A | 1/1985 | Blazek et al. | |
| 4,580,339 A * | 4/1986 | Ioffe | H01R 43/00 600/397 |
| 4,583,190 A | 4/1986 | Salb | |
| 4,583,549 A * | 4/1986 | Manoli | A61B 5/411 600/397 |
| 4,674,511 A | 6/1987 | Cartmell | |
| 4,803,992 A | 2/1989 | Lemelson | |
| 4,859,057 A | 8/1989 | Taylor et al. | |
| 4,869,254 A | 9/1989 | Stone et al. | |
| 4,880,304 A | 11/1989 | Jaeb et al. | |
| 4,890,622 A * | 1/1990 | Ferrari | A61B 5/259 600/395 |
| 4,902,886 A | 2/1990 | Smisko | |
| 4,934,372 A | 6/1990 | Corenman et al. | |
| 4,938,228 A | 7/1990 | Righter et al. | |
| 4,967,264 A | 10/1990 | Parulski et al. | |
| 5,025,791 A | 6/1991 | Niwa | |
| 5,184,620 A | 2/1993 | Cudahy et al. | |
| 5,203,329 A | 4/1993 | Takatani et al. | |
| 5,215,087 A * | 6/1993 | Anderson | A61B 5/259 600/397 |
| 5,224,486 A | 7/1993 | Lerman et al. | |
| 5,261,401 A | 11/1993 | Baker et al. | |
| 5,265,579 A | 11/1993 | Ferrari | |
| 5,307,818 A | 5/1994 | Segalowitz | |
| 5,372,125 A | 12/1994 | Lyons | |
| 5,419,321 A | 5/1995 | Evans | |
| 5,427,093 A | 6/1995 | Ogawa et al. | |
| 5,448,991 A | 9/1995 | Polson | |
| 5,465,715 A * | 11/1995 | Lyons | A61B 5/259 607/152 |
| 5,465,727 A | 11/1995 | Reinhold | |
| 5,511,553 A | 4/1996 | Segalowitz | |
| 5,549,116 A | 8/1996 | Mauer | |
| 5,632,272 A | 5/1997 | Diab et al. | |
| 5,673,692 A | 10/1997 | Schulze et al. | |
| 5,730,143 A | 3/1998 | Schwarzberg | |
| 5,779,631 A | 7/1998 | Chance | |
| 5,817,008 A | 10/1998 | Rafert et al. | |
| 5,912,703 A | 6/1999 | Tamayama | |
| 5,931,791 A | 8/1999 | Saltzstein et al. | |
| 5,938,597 A | 8/1999 | Stratbucker | |
| 5,971,930 A | 10/1999 | Elghazzawi | |
| 6,032,060 A | 2/2000 | Carim et al. | |
| 6,041,247 A | 3/2000 | Weckstrom | |
| 6,088,607 A | 7/2000 | Diab et al. | |
| 6,122,535 A | 9/2000 | Kaestle et al. | |
| 6,134,460 A | 10/2000 | Chance | |
| 6,263,222 B1 | 7/2001 | Diab et al. | |
| 6,327,487 B1 | 12/2001 | Stratbucker | |
| 6,385,473 B1 * | 5/2002 | Haines | A61B 5/0006 600/382 |
| 6,453,186 B1 | 9/2002 | Lovejoy et al. | |
| 6,525,386 B1 | 2/2003 | Mills | |
| 6,526,300 B1 | 2/2003 | Kiani et al. | |
| 6,569,095 B2 | 5/2003 | Eggers | |
| 6,647,287 B1 | 11/2003 | Peel et al. | |
| 6,662,033 B2 | 12/2003 | Casciani et al. | |
| 6,665,385 B2 | 12/2003 | Rogers et al. | |
| 6,694,177 B2 | 2/2004 | Eggers et al. | |
| 6,699,194 B1 | 3/2004 | Diab et al. | |
| 6,725,074 B1 | 4/2004 | Kaestle | |
| 6,745,061 B1 | 6/2004 | Hicks et al. | |
| 6,830,711 B2 | 6/2004 | Mills et al. | |
| 6,801,137 B2 | 10/2004 | Eggers | |
| 6,934,570 B2 | 8/2005 | Kiani et al. | |
| 6,940,403 B2 | 9/2005 | Kail, IV | |
| 7,018,338 B2 | 3/2006 | Vetter et al. | |
| 7,027,858 B2 | 4/2006 | Cao et al. | |
| 7,067,893 B2 | 6/2006 | Mills et al. | |
| 7,099,715 B2 | 8/2006 | Korzinov et al. | |
| 7,130,396 B2 | 10/2006 | Rogers et al. | |
| 7,194,300 B2 | 3/2007 | Korzinov | |
| 7,212,850 B2 | 5/2007 | Prystowsky | |
| 7,215,984 B2 | 5/2007 | Diab et al. | |
| 7,257,438 B2 | 8/2007 | Kinast | |
| 7,332,784 B2 | 2/2008 | Mills et al. | |
| 7,341,559 B2 | 3/2008 | Schulz et al. | |
| 7,412,282 B2 | 8/2008 | Houben | |
| 7,502,643 B2 | 3/2009 | Farringdon et al. | |
| 7,553,166 B2 | 6/2009 | Gobron | |
| 7,587,237 B2 | 9/2009 | Korzinov et al. | |
| 7,668,588 B2 | 2/2010 | Kovacs | |
| 7,729,753 B2 | 6/2010 | Kremliovsky et al. | |
| 7,831,301 B2 | 11/2010 | Webb et al. | |
| 7,881,765 B2 | 2/2011 | Mertz et al. | |
| D634,431 S | 3/2011 | Severe et al. | |
| 7,904,133 B2 | 3/2011 | Gehman et al. | |
| 7,907,996 B2 | 3/2011 | Prystowsky et al. | |
| 7,941,207 B2 | 5/2011 | Korzinov | |
| 7,962,202 B2 | 6/2011 | Bhunia | |
| 7,988,638 B2 | 8/2011 | Novae | |
| 8,116,841 B2 | 2/2012 | Bly et al. | |

(56) References Cited

U.S. PATENT DOCUMENTS

| | | |
|---|---|---|
| 8,145,287 B2 | 3/2012 | Diab et al. |
| 8,150,502 B2 | 4/2012 | Kumar et al. |
| 8,160,682 B2 | 4/2012 | Kumar et al. |
| D659,836 S | 5/2012 | Bensch et al. |
| 8,172,761 B1 | 5/2012 | Rulkov et al. |
| 8,200,319 B2 | 6/2012 | Pu et al. |
| 8,200,320 B2 | 6/2012 | Kovacs |
| 8,203,704 B2 | 6/2012 | Merritt et al. |
| 8,219,198 B2 | 7/2012 | Gollasch et al. |
| 8,249,686 B2 | 8/2012 | Libbus et al. |
| 8,271,072 B2 | 9/2012 | Houben et al. |
| RE43,767 E | 10/2012 | Eggers et al. |
| 8,285,356 B2 | 10/2012 | Bly et al. |
| 8,290,129 B2 | 10/2012 | Rogers et al. |
| 8,290,574 B2 | 10/2012 | Field et al. |
| 8,301,236 B2 | 10/2012 | Baumann et al. |
| 8,374,686 B2 | 2/2013 | Ghanem |
| 8,428,682 B1 | 4/2013 | Rood et al. |
| 8,452,364 B2 | 5/2013 | Hannula et al. |
| 8,460,189 B2 | 6/2013 | Libbus et al. |
| 8,473,039 B2 | 6/2013 | Michelson et al. |
| 8,473,047 B2 | 6/2013 | Chakravarthy et al. |
| 8,538,503 B2 | 9/2013 | Kumar et al. |
| 8,554,311 B2 | 10/2013 | Warmer et al. |
| 8,560,046 B2 | 10/2013 | Kumar et al. |
| 8,577,431 B2 | 11/2013 | Lamego et al. |
| 8,585,605 B2 | 11/2013 | Sola I Caros et al. |
| 8,591,430 B2 | 11/2013 | Amurthur et al. |
| D701,964 S | 4/2014 | Yoneta et al. |
| 8,688,190 B2 | 4/2014 | Libbus et al. |
| 8,718,752 B2 | 5/2014 | Libbus et al. |
| 8,731,649 B2 | 5/2014 | Lisogurski |
| 8,743,258 B2 | 6/2014 | Park et al. |
| 8,821,397 B2 | 9/2014 | Al-Ali et al. |
| 8,989,830 B2 | 3/2015 | LeBoeuf et al. |
| D738,757 S | 9/2015 | Cross et al. |
| D744,109 S | 11/2015 | Yoneta et al. |
| D744,110 S | 11/2015 | Kubo et al. |
| 9,186,112 B2 | 11/2015 | Bechtel et al. |
| 9,241,643 B2 | 1/2016 | Lisogurski |
| 9,277,864 B2 | 3/2016 | Yang et al. |
| 9,289,175 B2 | 3/2016 | LeBoeuf et al. |
| D760,903 S | 7/2016 | Lin et al. |
| 9,392,946 B1 | 7/2016 | Sarantos |
| 9,398,870 B2 | 7/2016 | Bechtel et al. |
| 9,506,802 B2 | 11/2016 | Chu et al. |
| D787,066 S | 5/2017 | Kim et al. |
| 9,636,057 B2 | 5/2017 | Scheuing et al. |
| 9,642,565 B2 | 5/2017 | Gonopolskiy et al. |
| 9,664,556 B2 | 5/2017 | Chu et al. |
| 9,696,199 B2 | 7/2017 | Chu et al. |
| 9,717,425 B2 | 8/2017 | Kiani et al. |
| 9,752,925 B2 | 9/2017 | Chu et al. |
| D800,313 S | 10/2017 | Chang |
| 9,775,548 B2 | 10/2017 | Sarantos et al. |
| 9,782,132 B2 | 10/2017 | Golda et al. |
| 9,801,547 B2 | 10/2017 | Yuen et al. |
| D810,944 S | 2/2018 | Goolkasian |
| 9,888,872 B2 | 2/2018 | Bechtel et al. |
| D812,229 S | 3/2018 | Al-Siddiq |
| 10,045,722 B2 | 8/2018 | Kintz et al. |
| 10,080,527 B2 | 9/2018 | Golda et al. |
| 10,088,356 B2 | 10/2018 | Chu et al. |
| 10,244,949 B2 | 4/2019 | Moyer et al. |
| D850,626 S | 6/2019 | Gardner et al. |
| D851,253 S | 6/2019 | Goolkasian |
| 10,413,251 B2 | 9/2019 | Golda et al. |
| D868,974 S | 12/2019 | Albert et al. |
| D868,977 S | 12/2019 | Vardi |
| D880,703 S | 4/2020 | Emery et al. |
| 10,610,159 B2 | 4/2020 | Eletr et al. |
| 10,824,391 B2 | 11/2020 | Savolainen et al. |
| 10,863,947 B2 | 12/2020 | Golda et al. |
| 10,959,678 B2 | 3/2021 | Golda et al. |
| 10,980,486 B2 | 4/2021 | Van Zandt Moyer et al. |
| D931,467 S | 9/2021 | Golda et al. |
| 11,185,291 B2 | 11/2021 | Eletr et al. |
| 2002/0026127 A1 | 2/2002 | Balbierz et al. |
| 2002/0038082 A1 | 3/2002 | Chin |
| 2002/0072685 A1 | 6/2002 | Rymut et al. |
| 2002/0180605 A1 | 12/2002 | Ozguz et al. |
| 2003/0055478 A1 | 3/2003 | Lyster |
| 2003/0065269 A1 | 4/2003 | Vetter et al. |
| 2003/0073916 A1 | 4/2003 | Yonce |
| 2003/0139654 A1 | 7/2003 | Kim et al. |
| 2003/0176795 A1 | 9/2003 | Harris et al. |
| 2003/0225322 A1 | 12/2003 | Uchiyama et al. |
| 2003/0225323 A1 | 12/2003 | Kiani et al. |
| 2004/0010201 A1 | 1/2004 | Korzinov et al. |
| 2004/0015091 A1 | 1/2004 | Greenwald et al. |
| 2004/0039419 A1 | 2/2004 | Stickney et al. |
| 2004/0039420 A1 | 2/2004 | Jayne et al. |
| 2004/0042581 A1 | 3/2004 | Okerlund |
| 2004/0054273 A1 | 3/2004 | Finneran et al. |
| 2004/0082842 A1 | 4/2004 | Lumba et al. |
| 2004/0082862 A1 | 4/2004 | Chance |
| 2004/0146149 A1 | 7/2004 | Rogers et al. |
| 2004/0260189 A1 | 12/2004 | Eggers et al. |
| 2005/0096557 A1 | 5/2005 | Vosburgh |
| 2005/0187446 A1 | 8/2005 | Nordstrom |
| 2005/0197549 A1 | 9/2005 | Baker, Jr. |
| 2005/0261559 A1 | 11/2005 | Mumford |
| 2005/0277841 A1 | 12/2005 | Shennib |
| 2005/0288726 A1 | 12/2005 | Gollasch |
| 2006/0056487 A1 | 3/2006 | Kuroda et al. |
| 2006/0167515 A1 | 7/2006 | Stickney et al. |
| 2006/0170649 A1 | 8/2006 | Kosugi et al. |
| 2006/0224072 A1 | 10/2006 | Shennib |
| 2007/0032719 A1 | 2/2007 | Menon et al. |
| 2007/0070800 A1 | 3/2007 | Virag et al. |
| 2007/0093705 A1 | 4/2007 | Shin et al. |
| 2007/0103296 A1 | 5/2007 | Paessel et al. |
| 2007/0106136 A1 | 5/2007 | Sterling et al. |
| 2007/0129642 A1 | 6/2007 | Korzinov |
| 2007/0130657 A1 | 6/2007 | Rogers et al. |
| 2007/0142715 A1 | 6/2007 | Banet et al. |
| 2007/0156054 A1 | 7/2007 | Korzinov et al. |
| 2007/0167850 A1 | 7/2007 | Russell et al. |
| 2007/0191723 A1 | 8/2007 | Prystowsky et al. |
| 2007/0191728 A1 | 8/2007 | Shennib |
| 2007/0206655 A1 | 9/2007 | Haslett et al. |
| 2007/0208542 A1 | 9/2007 | Vock et al. |
| 2007/0255156 A1 | 11/2007 | Mertz et al. |
| 2007/0255184 A1 | 11/2007 | Shennib |
| 2007/0282212 A1 | 12/2007 | Sierra et al. |
| 2007/0293776 A1 | 12/2007 | Korzinov et al. |
| 2008/0061846 A1 | 3/2008 | Kase et al. |
| 2008/0091090 A1 | 4/2008 | Guillory et al. |
| 2008/0101064 A1 | 5/2008 | Draganov |
| 2008/0139953 A1 | 6/2008 | Baker et al. |
| 2008/0288026 A1 | 11/2008 | Cross |
| 2008/0300641 A1 | 12/2008 | Brunekreeft et al. |
| 2009/0054742 A1 | 2/2009 | Kaminska |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0105602 A1 | 4/2009 | Gehman et al. |
| 2009/0171177 A1 | 7/2009 | Hannula et al. |
| 2009/0234410 A1 | 9/2009 | Libbus et al. |
| 2009/0290279 A1 | 11/2009 | Rodgriguez et al. |
| 2009/0306536 A1 | 12/2009 | Ranganathan et al. |
| 2010/0004518 A1 | 1/2010 | Vo et al. |
| 2010/0026995 A1 | 2/2010 | Merritt et al. |

(56) References Cited

U.S. PATENT DOCUMENTS

| | | |
|---|---|---|
| 2010/0030039 A1 | 2/2010 | Lamego |
| 2010/0054138 A1 | 3/2010 | Gips et al. |
| 2010/0134241 A1 | 6/2010 | Gips et al. |
| 2010/0160794 A1 | 6/2010 | Banet et al. |
| 2010/0179391 A1 | 7/2010 | Quintanar et al. |
| 2010/0191509 A1 | 7/2010 | Li et al. |
| 2010/0198044 A1 | 8/2010 | Gehman et al. |
| 2010/0204586 A1 | 8/2010 | Pu et al. |
| 2010/0204599 A1 | 8/2010 | Pu et al. |
| 2010/0249541 A1 | 9/2010 | Geva et al. |
| 2010/0262430 A1 | 10/2010 | Gips et al. |
| 2010/0268103 A1 | 10/2010 | Mcnamara et al. |
| 2010/0324387 A1 | 10/2010 | Moon et al. |
| 2010/0286495 A1 | 11/2010 | McGonigle et al. |
| 2010/0286532 A1 | 11/2010 | Farringdon et al. |
| 2010/0298655 A1 | 11/2010 | McCombie |
| 2010/0298656 A1 | 11/2010 | McCombie |
| 2010/0312188 A1 | 12/2010 | Robertson |
| 2010/0317937 A1 | 12/2010 | Kuhn et al. |
| 2010/0317942 A1 | 12/2010 | Cinbis et al. |
| 2010/0317947 A1 | 12/2010 | Cinbis et al. |
| 2010/0317958 A1 | 12/2010 | Beck et al. |
| 2010/0318146 A1 | 12/2010 | Cinbis et al. |
| 2010/0324389 A1 | 12/2010 | Moon et al. |
| 2011/0004106 A1 | 1/2011 | Iwamiya et al. |
| 2011/0021897 A1 | 1/2011 | Webb et al. |
| 2011/0066039 A1 | 3/2011 | Banet et al. |
| 2011/0066049 A1 | 3/2011 | Matsumoto |
| 2011/0066062 A1 | 3/2011 | Banet et al. |
| 2011/0098933 A1 | 4/2011 | Ochs |
| 2011/0105860 A1 | 5/2011 | Houben et al. |
| 2011/0105926 A1 | 5/2011 | Kornet |
| 2011/0124979 A1 | 5/2011 | Heneghan |
| 2011/0125040 A1 | 5/2011 | Crawford et al. |
| 2011/0144470 A1 | 6/2011 | Mazar et al. |
| 2011/0158284 A1 | 6/2011 | Goto |
| 2011/0160604 A1 | 6/2011 | Istvan et al. |
| 2011/0166434 A1 | 7/2011 | Gargiulo |
| 2011/0166468 A1 | 7/2011 | Prystowsky et al. |
| 2011/0190598 A1 | 8/2011 | Shusterman |
| 2011/0194007 A1 | 8/2011 | Kim et al. |
| 2011/0208076 A1 | 8/2011 | Fong et al. |
| 2011/0208078 A1 | 8/2011 | Cho et al. |
| 2011/0263994 A1 | 10/2011 | Burns |
| 2011/0270049 A1 | 11/2011 | Katra et al. |
| 2011/0270112 A1 | 11/2011 | Manera et al. |
| 2011/0279963 A1 | 11/2011 | Kumar |
| 2011/0301445 A9 | 12/2011 | Webb et al. |
| 2011/0301493 A1 | 12/2011 | Husheer |
| 2012/0016245 A1 | 1/2012 | Niwa et al. |
| 2012/0029306 A1 | 2/2012 | Paquet |
| 2012/0029320 A1 | 2/2012 | Watson et al. |
| 2012/0035490 A1 | 2/2012 | Shen et al. |
| 2012/0035494 A1 | 2/2012 | Chakravarthy et al. |
| 2012/0061695 A1 | 3/2012 | Kim |
| 2012/0071744 A1 | 3/2012 | Euliano et al. |
| 2012/0083673 A1 | 4/2012 | Al-Ali et al. |
| 2012/0101396 A1 | 4/2012 | Solosko et al. |
| 2012/0108917 A1 | 5/2012 | Libbus et al. |
| 2012/0108920 A1 | 5/2012 | Bly et al. |
| 2012/0109572 A1 | 5/2012 | Shimizu |
| 2012/0110226 A1 | 5/2012 | Mach et al. |
| 2012/0110228 A1 | 5/2012 | Mach et al. |
| 2012/0136226 A1 | 5/2012 | Wilke |
| 2012/0143079 A1 | 6/2012 | Lia et al. |
| 2012/0176599 A1 | 7/2012 | Leung |
| 2012/0197150 A1 | 8/2012 | Cao et al. |
| 2012/0203077 A1 | 8/2012 | He et al. |
| 2012/0204068 A1 | 8/2012 | Ye et al. |
| 2012/0226129 A1 | 9/2012 | Callahan et al. |
| 2012/0232369 A1 | 9/2012 | Kim et al. |
| 2012/0245951 A1 | 9/2012 | Gips et al. |
| 2012/0277549 A1 | 11/2012 | Libbus et al. |
| 2012/0284003 A1 | 11/2012 | Gosh |
| 2012/0289839 A1 | 11/2012 | Takenoshita |
| 2012/0330126 A1 | 12/2012 | Hoppe |
| 2012/0330151 A1 | 12/2012 | Weinstein et al. |
| 2013/0012938 A1 | 1/2013 | Asirvatham |
| 2013/0030257 A1 | 1/2013 | Nakata |
| 2013/0030259 A1 | 1/2013 | Thomsen et al. |
| 2013/0085347 A1 | 4/2013 | Manicka et al. |
| 2013/0085708 A1 | 4/2013 | Sattler |
| 2013/0096395 A1 | 4/2013 | Katra et al. |
| 2013/0116520 A1 | 5/2013 | Roham |
| 2013/0116534 A1 | 5/2013 | Woo |
| 2013/0116585 A1 | 5/2013 | Bouguerra |
| 2013/0144130 A1 | 6/2013 | Russell et al. |
| 2013/0158372 A1 | 6/2013 | Haisley |
| 2013/0172724 A1 | 7/2013 | Aziz et al. |
| 2013/0225938 A1 | 8/2013 | Mach |
| 2013/0245388 A1 | 9/2013 | Rafferty et al. |
| 2013/0245415 A1 | 9/2013 | Kumar et al. |
| 2013/0253285 A1 | 9/2013 | Bly et al. |
| 2013/0261422 A1 | 10/2013 | Gilmore et al. |
| 2013/0267854 A1 | 10/2013 | Johnson et al. |
| 2013/0296660 A1 | 11/2013 | Tsien |
| 2013/0296823 A1 | 11/2013 | Melker |
| 2013/0324812 A1 | 12/2013 | Brainard |
| 2013/0324816 A1 | 12/2013 | Bechtel et al. |
| 2013/0324855 A1 | 12/2013 | Lisogurski |
| 2013/0331665 A1 | 12/2013 | Libbus et al. |
| 2013/0338448 A1 | 12/2013 | Libbus et al. |
| 2013/0338460 A1 | 12/2013 | He et al. |
| 2014/0038147 A1 | 2/2014 | Morrow |
| 2014/0066726 A1 * | 3/2014 | Costello ............ A61B 5/0028 600/573 |
| 2014/0066732 A1 | 3/2014 | Addison et al. |
| 2014/0066783 A1 | 3/2014 | Kiani et al. |
| 2014/0081152 A1 | 3/2014 | Clinton |
| 2014/0091926 A1 | 4/2014 | Gips et al. |
| 2014/0100432 A1 | 4/2014 | Golda et al. |
| 2014/0121557 A1 | 5/2014 | Gannon et al. |
| 2014/0206976 A1 | 7/2014 | Thompson |
| 2014/0228656 A1 | 8/2014 | Gonopolskiy et al. |
| 2014/0275869 A1 | 9/2014 | Kintz et al. |
| 2014/0276089 A1 | 9/2014 | Kirenko et al. |
| 2015/0057511 A1 | 2/2015 | Basu |
| 2015/0087948 A1 | 3/2015 | Bishay et al. |
| 2015/0087951 A1 | 3/2015 | Felix et al. |
| 2015/0094551 A1 | 4/2015 | Frix et al. |
| 2015/0094552 A1 | 4/2015 | Golda et al. |
| 2015/0148622 A1 | 5/2015 | Moyer et al. |
| 2015/0148637 A1 | 5/2015 | Golda et al. |
| 2015/0148691 A1 | 5/2015 | Moyer et al. |
| 2015/0335288 A1 | 11/2015 | Toth et al. |
| 2015/0351690 A1 | 12/2015 | Toth et al. |
| 2016/0073954 A1 | 3/2016 | Meitav |
| 2016/0238440 A1 | 8/2016 | Chu et al. |
| 2016/0302674 A1 | 10/2016 | Moyer et al. |
| 2016/0345881 A1 | 12/2016 | Sarantos et al. |
| 2017/0027513 A1 | 2/2017 | Mulpuru |
| 2017/0095156 A1 | 4/2017 | Richards |
| 2017/0337412 A1 | 11/2017 | Bhat et al. |
| 2017/0337413 A1 | 11/2017 | Bhat et al. |
| 2018/0028122 A1 | 2/2018 | Golda et al. |
| 2018/0085068 A1 | 3/2018 | Telfort |
| 2018/0177459 A1 | 6/2018 | Eletr et al. |
| 2018/0325385 A1 | 11/2018 | Deterding et al. |
| 2019/0029599 A1 | 1/2019 | Golda et al. |
| 2019/0282096 A1 | 9/2019 | Vardi |
| 2019/0320914 A1 | 10/2019 | Moyer et al. |
| 2020/0008749 A1 | 1/2020 | Golda et al. |
| 2020/0229767 A1 | 7/2020 | Eletr et al. |
| 2020/0237309 A1 | 7/2020 | Golda et al. |
| 2021/0059586 A1 | 3/2021 | Marriott et al. |
| 2021/0100514 A1 | 4/2021 | Golda et al. |
| 2021/0145293 A1 | 5/2021 | Van Zandt Moyer et al. |
| 2021/0236064 A1 | 8/2021 | Van Zandt Moyer et al. |

FOREIGN PATENT DOCUMENTS

| | | |
|---|---|---|
| CN | 201641985 U | 11/2010 |
| CN | 101984743 A | 3/2011 |
| CN | 102215747 A | 10/2011 |

(56) References Cited

FOREIGN PATENT DOCUMENTS

| | | |
|---|---|---|
| CN | 202288274 U | 7/2012 |
| CN | 105997103 A | 10/2016 |
| CN | 104812296 B | 5/2018 |
| EP | 0581073 A2 | 2/1994 |
| EP | 1737337 B1 | 5/2005 |
| EP | 1139858 B1 | 4/2007 |
| EP | 2438851 A2 | 4/2012 |
| EP | 2305103 B1 | 9/2013 |
| EP | 2903509 B1 | 9/2019 |
| EP | 3636148 A1 | 4/2020 |
| EP | 3099224 B1 | 5/2020 |
| EP | 3636148 A3 | 5/2020 |
| EP | 3769669 A1 | 1/2021 |
| JP | 52-052494 | 4/1977 |
| JP | 52052494 | 4/1977 |
| JP | 02172443 A | 7/1990 |
| JP | H05123305 A | 5/1993 |
| JP | H07213630 A | 8/1995 |
| JP | H09224917 A | 9/1997 |
| JP | 2001029318 A | 2/2001 |
| JP | 2001078974 A | 3/2001 |
| JP | 2002125944 A | 5/2002 |
| JP | 2002263075 A | 9/2002 |
| JP | 2004000474 | 1/2004 |
| JP | 2004016248 A | 1/2004 |
| JP | 2006000481 A | 1/2006 |
| JP | 2006158813 A | 6/2006 |
| JP | 3952082 B2 | 8/2007 |
| JP | 2007244531 A | 9/2007 |
| JP | 2007296266 A | 11/2007 |
| JP | 2011147746 A | 8/2011 |
| JP | 20120187404 A | 10/2012 |
| JP | 5408751 B2 | 2/2014 |
| JP | 6298063 B2 | 3/2018 |
| JP | 6539827 B2 | 7/2019 |
| JP | 6625682 B2 | 12/2019 |
| JP | 2020513876 A | 5/2020 |
| WO | W09401039 A1 | 1/1994 |
| WO | WO9427494 A1 | 12/1994 |
| WO | WO0045696 A1 | 8/2000 |
| WO | WO0059374 A1 | 10/2000 |
| WO | WO01/043624 A4 | 6/2001 |
| WO | WO2001085019 A2 | 11/2001 |
| WO | WO2001093758 A1 | 12/2001 |
| WO | W00200094 A2 | 1/2002 |
| WO | WO2002085201 A1 | 10/2002 |
| WO | WO2002086792 A2 | 10/2002 |
| WO | WO2002086835 A1 | 10/2002 |
| WO | WO2002086837 A1 | 10/2002 |
| WO | WO2003077752 A1 | 9/2003 |
| WO | WO2005079429 A2 | 1/2005 |
| WO | WO2005060829 A1 | 7/2005 |
| WO | WO2005072237 A2 | 8/2005 |
| WO | W02006014806 A2 | 2/2006 |
| WO | WO2006044919 A2 | 4/2006 |
| WO | WO2006110488 A2 | 10/2006 |
| WO | W02006124788 A2 | 11/2006 |
| WO | WO2006124788 A2 | 11/2006 |
| WO | 2008092098 A2 | 7/2008 |
| WO | WO2008092098 A2 | 7/2008 |
| WO | WO2008092098 A3 | 10/2008 |
| WO | WO2009036321 A1 | 3/2009 |
| WO | WO2009036327 A1 | 3/2009 |
| WO | 2009112972 A2 | 9/2009 |
| WO | WO2010/055155 A2 | 5/2010 |
| WO | WO2010093900 A2 | 8/2010 |
| WO | WO2010104952 A2 | 9/2010 |
| WO | WO2010107913 A2 | 9/2010 |
| WO | W02011074004 A2 | 6/2011 |
| WO | WO2012104658 A2 | 8/2012 |
| WO | WO2012129498 A1 | 9/2012 |
| WO | WO2012150563 A1 | 11/2012 |
| WO | 2014027293 A2 | 2/2014 |
| WO | 2014027293 A3 | 2/2014 |
| WO | 2014055994 A1 | 4/2014 |
| WO | 2015113054 A1 | 7/2015 |
| WO | WO2013/071014 A2 | 5/2016 |
| WO | 2016210334 A1 | 12/2016 |
| WO | WO2018112401 A1 | 6/2018 |
| WO | 2020154697 A1 | 7/2020 |

OTHER PUBLICATIONS

Palreddy, Surekha, Chapter 9—Signal Processing Algorithms, Design of Pulse Oximeters, Medical Science Series, Bristol [U.A.]; Institute of Physics Pub, GB, Jan. 1, 1997, pp. 124-158, 133-157, Taylor & Francis Group, LLC., New York, NY and Milton Park, Abingdon, Oxon, England.

International Search Report and Written Opinion of the International Searching Authority. International Application No. PCT/US20/15099 issued by the United State Patent Office, dated Jun. 4, 2020, 11 pages, Alexandria Virginia.

Yoo, Jerald et al., A 5.2 mW Self-Configured Wearable Body Sensor Network controller and a 12 uW Wirelessly Powered Sensor for a Continuous Health Monitoring System, IEEE Journal of Solid-State Circuits, Jan. 2010, pp. 178-188, vol. 45, Issue No. 1, Institute of Electrical and Electronics Engineers, Piscataway, NJ.

Partial European Search Report for Application No. 19194996.5 issued by the European Patent Office, dated Feb. 6, 2020, 15 pages, EPO, Munich, Germany.

Extended European Search Report including the Supplementary European Search Report (SESR) for Application No. EP13843561.5 issued by the European Patent Office, Munich, Germany dated Apr. 29, 2016.

Kadota, Hiroshi, Japanese Patent Office, Japanese Office Action dated Nov. 30, 2021 for Japanese Application No. 2020-218861, original 3 pages, and translation 3 pages; Japanese Patent Office.

Supplementary European Search Report for Application No. EP16815429 issued by the European Patent Office, dated Jan. 17, 2019, 4 pages, EPO, Munich, Germany.

Allen, John, Photoplethysmography and its application in clinical physiological measurement, Physiological Measurement, Feb. 20, 2007, pp. R1-R39, vol. 28, No. 3, IOP Publishing Ltd., Bristol, United Kingdom.

International Search Report and Written Opinion of the International Searching Authority. International Application No. PCT/US2016/039374 issued by the United State Patent Office, dated Oct. 28, 2016, 14 pages, Alexandria Virginia. (needs to be cited 101, 201, 301, 401, 701).

International Search Report and Written Opinion of the International Searching Authority. International Application No. PCT/US2013/063748 issued by the United State Patent Office, dated Feb. 27, 2014, 15 pages, Alexandria Virginia.

Timmerman, Luke, Xconomy, Inc., "UW Spinout Cardiac Insight Wins FDA OK for Heartbeat Monitor", published Jun. 6, 2013; website accessed Oct. 27, 2013, http://www.xconomy.com/seattle/2013/06/06/uw-spinout-cardiac-insight-wins-fda-ok-for-heartbeat-monitor/, Xconomy Inc., Cambridge, Massachusetts.

CardioNet, Inc., "CardioNet, Inc. Announces Launch of MCOTos 2:1 Device", published Jun. 19, 2013; website accessed Oct. 27, 2013, https://www.cardionet.com/index.htm, BioTelemetry, Inc., Conshohocken, Pennsylvania.

Heart Check, "The HeartCheck Pen, a Handheld ECG with Smart Monitoring", website accessed Oct. 27, 2013, http://heartcheckpen.com/, HeartCheckPEN.com, TAW Global, LLC, Portage, Michigan; CardioComm Solutions Inc., Toronto, ON, and Victoria, BC.

Corventis, Inc., "Nuvant Mobile Cardiac Telemetry", Copyright 2009-2013; website accessed Oct. 27, 2013, http://corventis.com/, Corventis, San Jose, California.

Transmittal of International Preliminary Report on Patentability dated of Apr. 16, 2015 and International Preliminary Report on Patentability dated Apr. 7, 2015 with Written Opinion of the International Searching Authority International Application No. PCT/US2013/063748 issued by the United State Patent Office, dated Feb. 27, 2014, 5 pages, Alexandria, Virginia.

International Search Report and Written Opinion of the International Searching Authority. International Application No. PCT/

(56) References Cited

OTHER PUBLICATIONS

US2015/13113 issued by the United State Patent Office, dated Jun. 29, 2015, 14 pages, Alexandria Virginia.

Kansy, Robert J., Response of a Correlated Double Sampling Circuity to 1/f Noise, IEEE Journal of Solid-State Circuits, Jun. 1980, pp. 373-375, vol. SC-15, No. 3, IEEE, New York, NY, USA.

Chinese Office Action, Application No. 201780077645.7, dated Jun. 15, 2021, China National Intellectual Property Administration, Beijing, China.

International Search Report and Written Opinion of the International Searching Authority. International Application No. PCT/US2020/048603 issued by the United States Patent Office, dated Jan. 4, 2020, 18 pages, USPTO, Alexandria, Virginia, USA.

Supplementary European Search Report for Application No. EP17880188 issued by the European Patent Office, dated Aug. 5, 2020, 8 pages, EPO, Munich, Germany.

Extended European Search Report for Application No. EP20175192 issued by the European Patent Office, dated Oct. 26, 2020, 12 pages, EPO, Munich, Germany.

Japanese Office Action dated Aug. 31, 2021 for Japanese Application No. 2019531741—original and translation.

PDF "Dictionary_composite" from https://www.merriam-webster.com/dictionary/composite accessed on Feb. 12, 2019 (Year:2019).

Extended European Search Report including the Supplementary European Search Report for Application No. EP15740972 issued by the European Patent Office, Munich, Germany dated Aug. 29, 2017.

Notification of transmiital of the International Search Report and the Written Opinion of the International Searching Authority for Application No. PCT/US2017/066805 issued by the International Searching Authority, Alexandria, VA dated Mar. 12, 2018, 1 page, which includes: The International Search Report completed Feb. 7, 2018 dated Mar. 12, 2018, 5 pages, with Written Opinion of the International Searching Authority for International Application No. PCT/US2017/066805 dated Mar. 12, 2018 issued by the United States Patent Office, Alexandria, Virginia, US.

Transmittal of International Preliminary Report of Patentability and International Preliminary Report on Patentability for Application No. PCT/US2016/039374 issued by the International Bureau of WIPO, Geneva, Switzerland dated Jan. 4, 2018 which includes: The International Preliminary Report on Patentability dated Dec. 26, 2017 with Written Opinion of the International Searching Authority for International Application No. PCT/US2016/039374 dated Oct. 28, 2016 issued by the United States Patent Office, Alexandria, Virginia, US.

\* cited by examiner

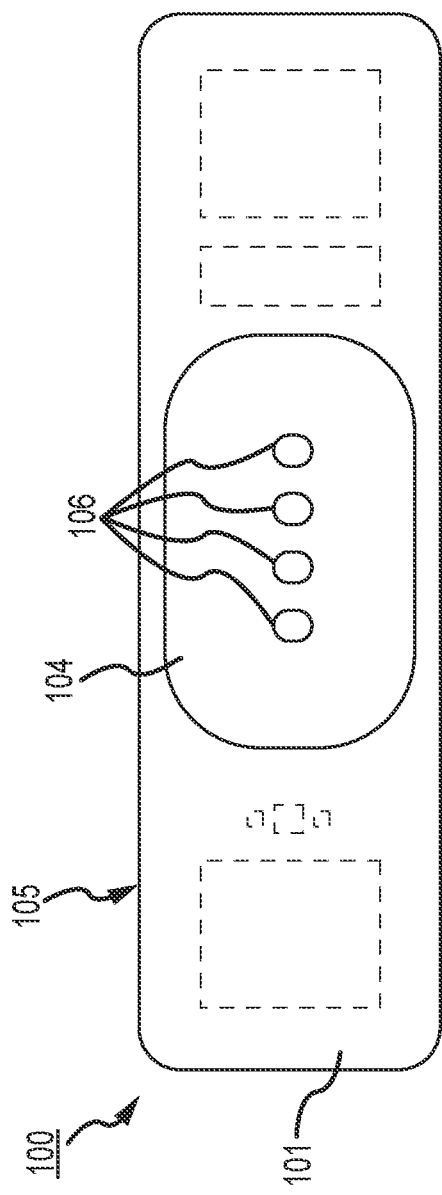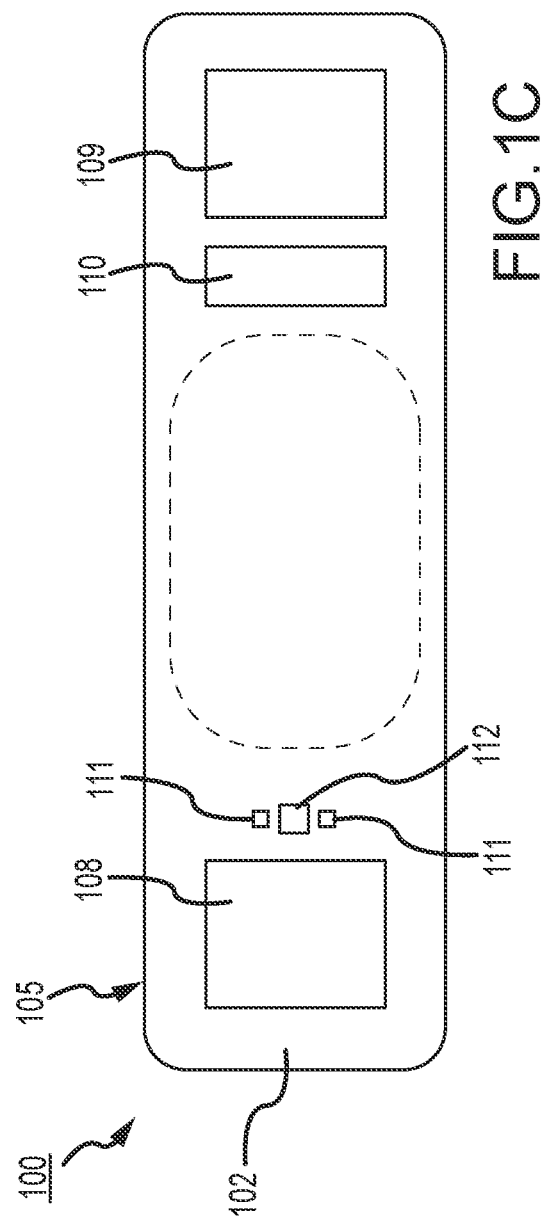

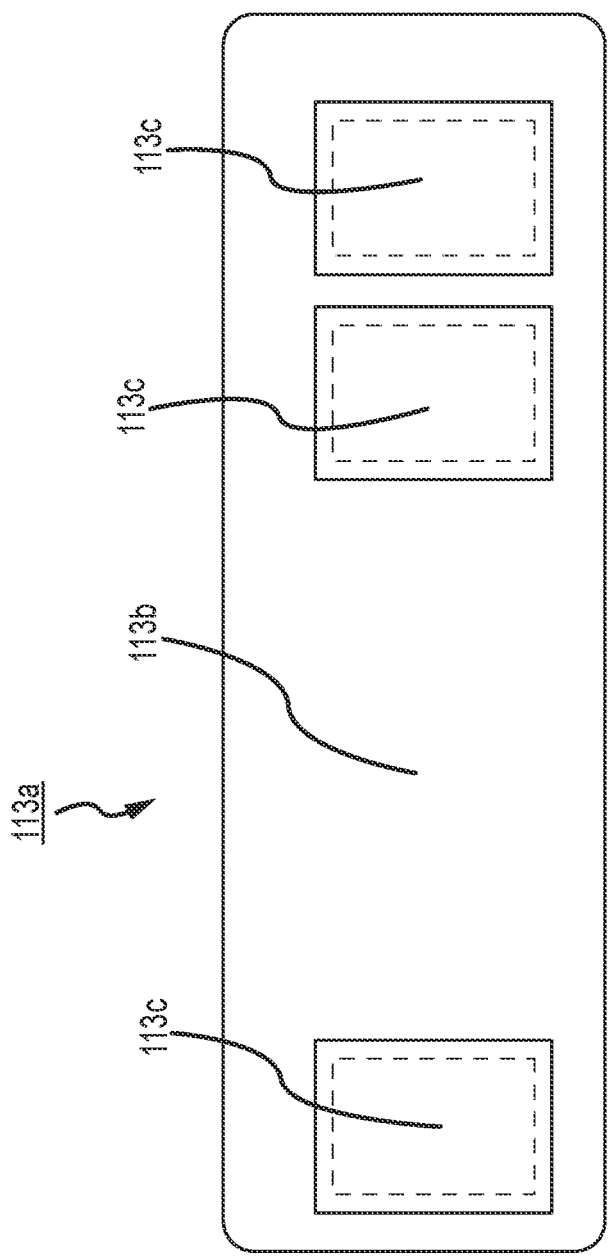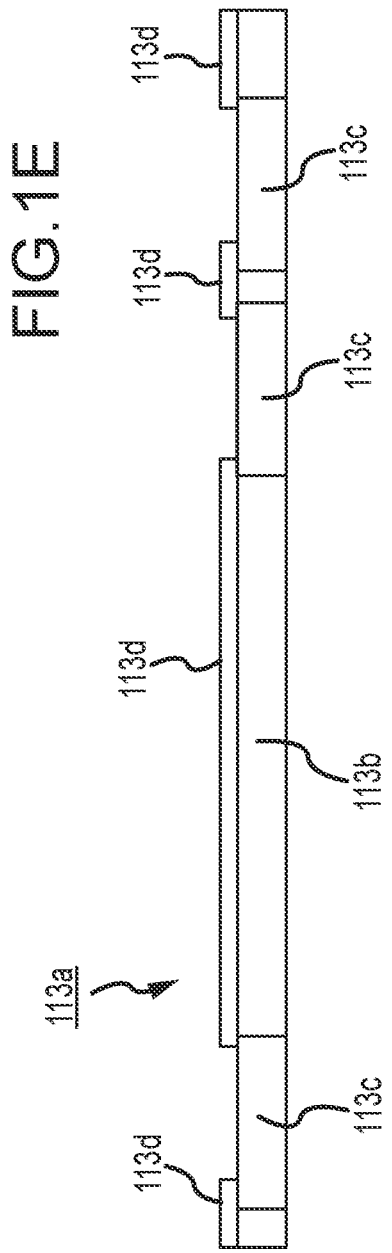

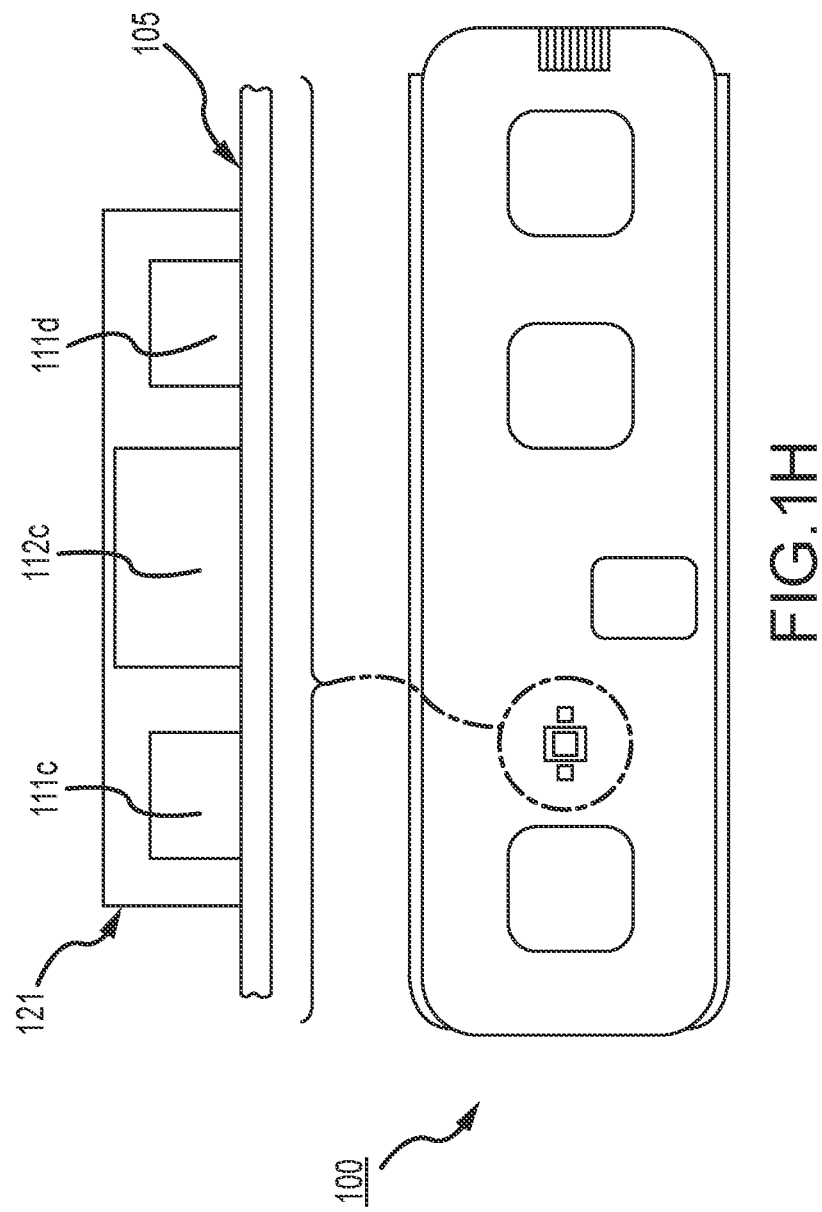

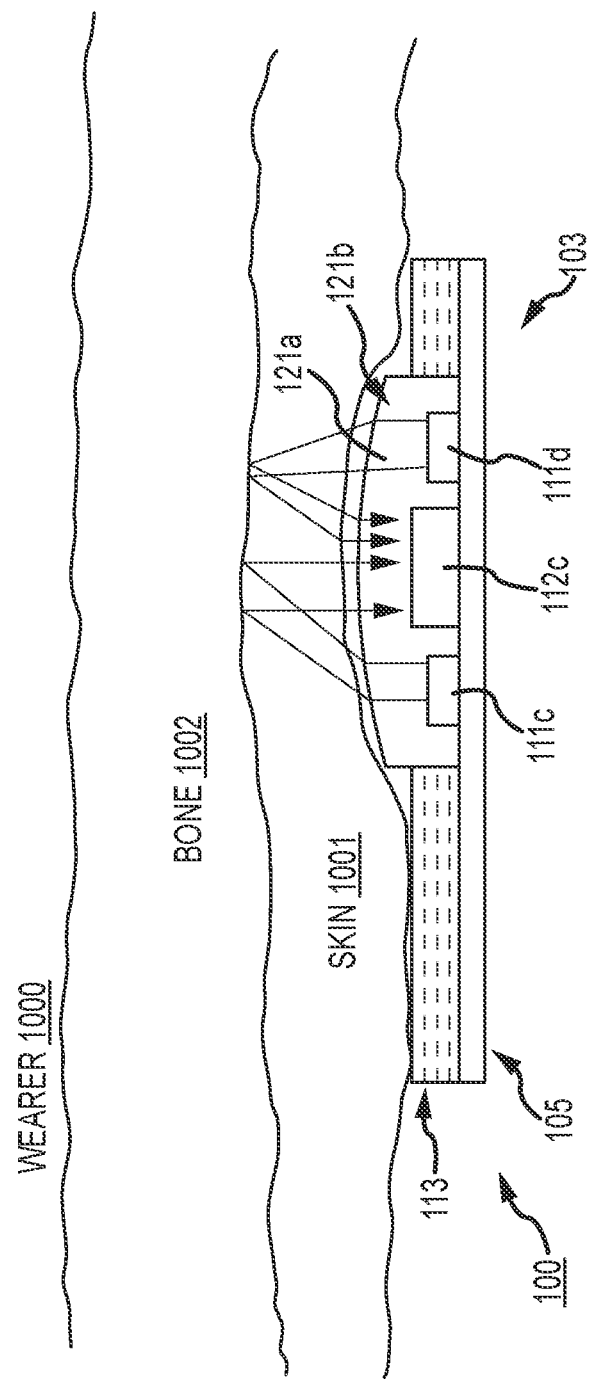

HEALTH MONITORING SYSTEMS AND METHODS

BACKGROUND

Advances in software, electronics, sensor technology and materials science have revolutionized patient monitoring technologies. In particular, many devices and systems are becoming available for a variety of health monitoring applications. However, improvements may yet be desired for health monitoring devices and systems that provide one or more of effective data collection and/or manipulation for parameter determination.

Further alternatives for patients and their physicians may then be developed to include robust and convenient monitors that in some instances may collect and transfer long-term data as well as monitor events in real-time, including multi-variable parameter determination.

SUMMARY

Described herein are several alternative medical monitoring devices, systems and/or methods for parameter determination, in some instances for long-term sensing and/or recording of cardiac and/or respiratory data of an individual, such as a neonate, athlete, or cardiac patient. A number of alternative implementations and applications are summarized and/or exemplified herein below and throughout this specification.

In one alternative aspect, the developments hereof may include an implementation wherein a health device is configured for monitoring a plurality of physiological parameters of an individual from time-concordant measurements collected by one or a plurality of sensors, including a variety of one or more of, but not limited to, electrodes for measuring ionic potential changes for electrocardiograms (ECGs), a light source and one or more photodetectors, such as LED-photodiode pairs, for optically based oxygen saturation measurements, a temperature sensor, an xyz accelerometer for movement and exertion measurements, and the like. In some implementations, methods and devices of the developments hereof may be used to generate a respiration waveform. Other implementations may include a circuit that mimics a driven right-leg circuit (sometimes referred to herein as "a proxy driven right-leg circuit") that may permit reduction in common mode noise in a small-footprint device conveniently adhered or having the capacity to be adhered to an individual.

In another alternative aspect hereof, a blood pressure determination may be made from a determination of pulse transit time. The pulse transit time is the time for the cardiac pressure wave to travel from the heart to other locations in the body. Measurements of pulse transit time may then be used to estimate blood pressure. Heart beat timing from ECG or otherwise and photoplethysmogram (aka PPG) signals can be used to generate pulse transit time. Note, such signals may be generated from conventional or other to-be-developed processes and/or devices or systems; or, such signals may be taken from one or more wearable health monitoring devices such as those also described hereinbelow.

In another alternative aspect, the developments hereof may include one or more methods and/or devices for measuring and/or determining oxygen saturation parameters from time concordant pulse oximetry signals and ECG signals. In one implementation, ECG signals may be used to define intervals, or "frames" of pulse oximetry data that are collected and averaged for determining the constant and main periodic components (e.g., DC and AC components) of the pulse oximetry signals from which, in turn, values for oxygen saturation may be determined. Patient-wearable devices of such implementations with pulse oximetry and ECG sensors may be particularly useful when placed on a patient's chest for such signal acquisition.

These as well as other alternative and/or additional aspects are exemplified in a number of illustrated alternative and/or additional implementations and applications, some of which are shown in the figures and characterized in the claims section that follows. However, as will be understood by the ordinarily skilled artisan, the above summary and the detailed description below do not describe the entire scope of the inventions hereof and are indeed not intended to describe each illustrated embodiment or every implementation of the present inventions nor provide any limitation on the claims or scope of protection herein set forth below.

BRIEF DESCRIPTION OF THE DRAWINGS

The drawings include:

FIG. 1, which includes and is defined by sub-part FIGS. 1A-1K, illustrates several alternatives of the present developments, including a variety of isometric, top and bottom plan and elevational views of devices and alternative conductive adhesive structures.

DETAILED DESCRIPTION

Figure 1A:
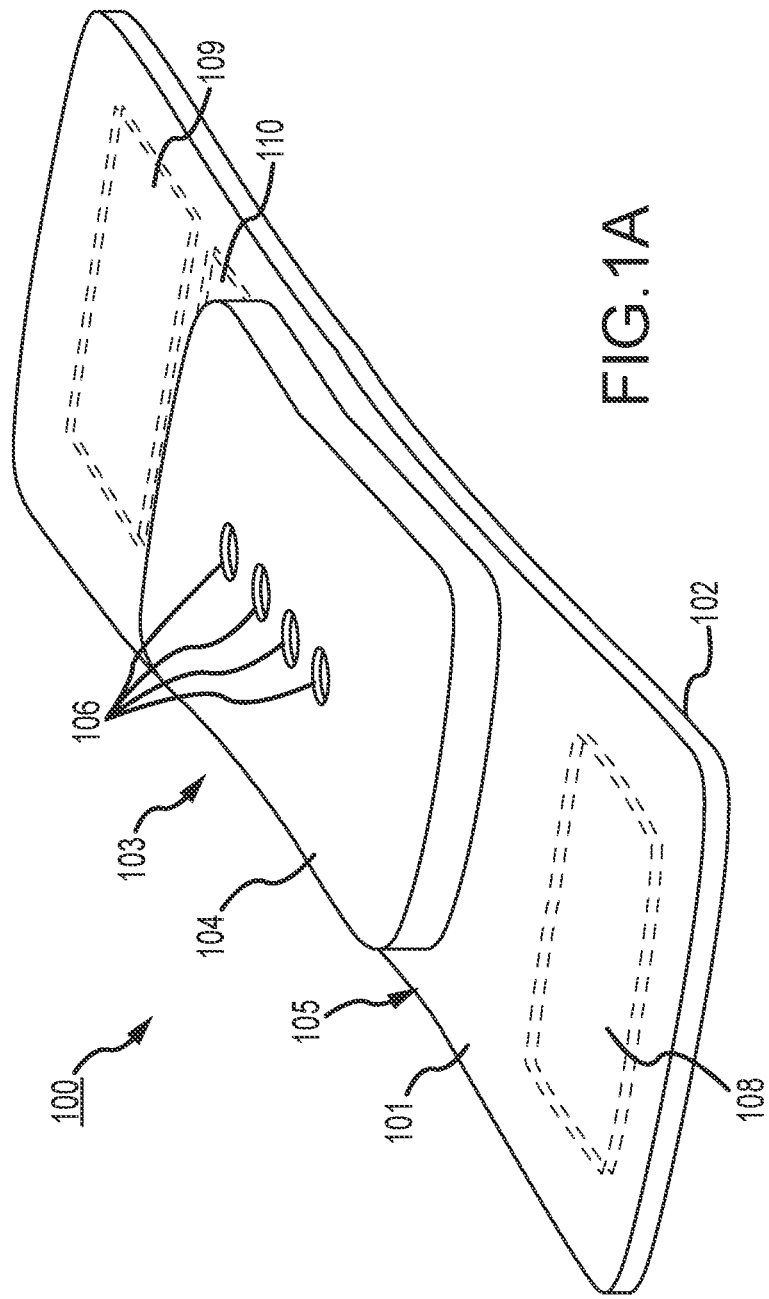

While the inventions hereof are amenable to various modifications and alternative forms, specifics thereof have been shown herein by way of example in the drawings and the following description. It should be understood, however, that the intention is not to limit the inventions to the particular embodiments described. The intention is to cover all modifications, equivalents, and alternatives falling within the spirit and scope of the inventions whether described here or otherwise being sufficiently appreciable as included herewithin even if beyond the literal words hereof.

In one aspect, a system hereof may include a device for monitoring physiological parameters such as one or more or all of electrocardiogram (aka ECG or EKG), photoplethysmogram (aka PPG), pulse oximetry, temperature and/or patient acceleration or movement signals.

Moreover, systems hereof may be established to measure and/or process such signals of a patient using or including one or more of the following elements: (a) a circuit, sometimes flexible as in or on or forming a flexible or flex circuit board, embedded in or on a flat elastic substrate or board having a top surface and a bottom surface, the circuit having one or more of (i) at least one sensor mounted in or on or adjacent the bottom surface of the flat elastic substrate, the at least one sensor being capable of electrical or optical communication with the patient, (ii) at least one signal processing module for receiving and/or accepting signals from the at least one sensor in some implementations also providing for transforming such signals for storage as patient data; (iii) at least one memory module for receiving and/or accepting and storing patient data, (iv) at least one data communication module for transferring patient data, stored or otherwise to an external device, and (v) a control module for controlling the timing and operation of the at least one sensor, one or more of the at least one signal processing module, the at least one memory module, the at least one data communication module, and/or the control module capable of receiving commands to implement transfer of patient data by the at least one data communication module and to erase and/or wipe patient data from the at least one memory module; and (b) a conductive adhesive removably attached to the bottom surface of the flat elastic substrate, the conductive adhesive capable of adhering to skin of the patient and of conducting an electrical signal substantially only in a direction perpendicular to the bottom surface of the flat elastic substrate, and/or in some implementations including a conductive portion adjacent the sensor or sensors and a non-conductive portion. In some implementations, the conductive adhesive is an anisotropically conductive adhesive in that it comprises regions of material that conducts current substantially only in a direction perpendicular to the skin (i.e. "z-axis" conduction).

In some implementations, devices hereof will be for comprehensive long-term cardiac monitoring, inter alia. Features of such may include one or more of a Lead 1 ECG, PPG, pulse oximeter, accelerometer, temperature sensor and/or a button or other indicator for manual patient event marking. Such a device may be adapted to store up to, for example, about two weeks of continuous data (though more or less will also be feasible in alternative implementations), which may in some implementations be downloaded to a clinic or other computer in a short time period, as for one example, in only about 90 seconds (though more or less time will be viable in alternative implementations) via computer connection, whether wireless or wired as in one example by USB or other acceptable data connection. A companion software data analysis package may be adapted to provide automated event capture and/or allow immediate or delayed, local data interpretation.

Intermittent cardiac anomalies are often difficult for physicians to detect and/or diagnose, as they would typically have to occur during a physical examination of the patient. A device hereof may address this problem with what in some implementations may be a continuous or substantially continuous monitoring of one or a number of vital signs.

Some alternative features may include one or more of (i) a driven "Right Leg" circuit with electrodes located only on the chest, (ii) a "z-Axis" or anisotropic conductive adhesive electrode interface that may permit electrical communication only between an electrode and a patient's skin immediately beneath the electrode, (iii) data transmission to and interpretation by a local computer accessible to CCU/ICU personnel, (iv) a unique combination of hardware that may allow correlation of multiple data sources in time concordance to aid in diagnosis.

In some alternative implementations, devices and systems hereof may provide 1) reusability (in some cases near or greater than about 1000 patients) that may allow recouping cost of the device in just about 10-15 patient tests; 2) one or more of ECG waveform data, inertial exertion sensing, manual event marking, temperature sensing and/or pulse oximetry, any or all of which in time concordance to better detect and analyze arrhythmic events; 3) efficient watertightness or waterproofing (for the patient/wearer to be able to swim while wearing the device); and 4) a comprehensive analysis package for typically immediate, local data interpretation. An alternative device may be adapted to take advantage of flex-circuit technology, to provide a device that is light-weight, thin, durable, and flexible to conform to and move with the patient's skin during patient/wearer movement.

FIGS. 1 and 2 illustrate examples of alternative implementations of devices that may be so adapted.

FIG. 1 shows a device 100 that has a component side or top side 101, patient side or circuit side 102, and one or more inner electrical layer(s), generally identified by the reference 103 and an elongated strip layer 105. The strip layer 105 may have electronics thereon and/or therewithin. FIG. 1A shows isometrically these in what may here be considered a substantially transparent device together with some other elements that may be used herewith. FIG. 1B is more specifically directed to a top side 101 plan view and FIG. 1C to an underside, patient side 102 plan view and FIG. 1D a first elevational, side view.

Figure 1D:
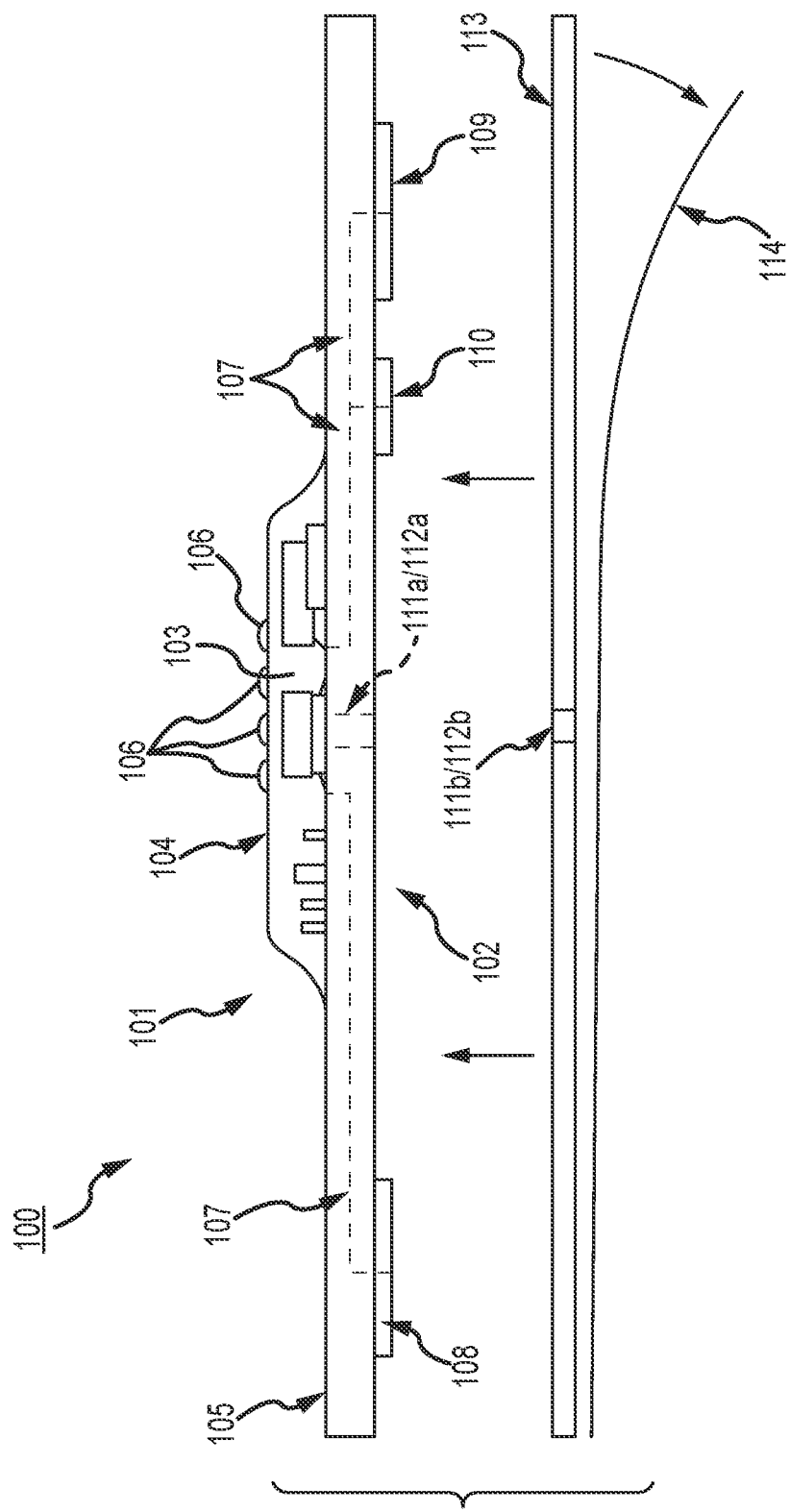

Many of the electronics hereof may be disposed in the electronics layer or layers 103, and as generally indicated here, the electronics may be encapsulated in a material 104 (see FIGS. 1A, 1B, 1D and 1K for some examples), medical grade silicone, plastic or the like, or potting material, to fix them in operative position on or in or otherwise functionally disposed relative to the elongated strip layer 105. The potting or other material may in many implementations also or alternatively provide a waterproof or watertight or water resistant coverage of the electronics to keep them operative even in water or sweat usage environments. One or more access points, junctions or other functional units 106 may be provided on and/or through any side of the encapsulation material 104 for exterior access and/or communication with the electronics disposed therewithin, or thereunder. FIGS. 1A, 1B and 1D show four such accesses 106 on the top side. These may include high Z data communication ports and/or charging contacts, inter alia. This upper or component side 101 of device 100 may be coated in a silicone compound for protection and/or waterproofing, with only, in some examples, a HS USB connector exposed via one or more ports 106, e.g., for data communication or transfer and/or for charging.

The elongated strip layer 105 may be or may include a circuit or circuit portions such as electrical leads or other inner layer conductors, e.g., leads 107 shown in FIG. 1D, for communication between the electronics 103 and the electrically conductive pads or contacts 108, 109 and 110 described further below (108 and 109 being in some examples, high impedance/high Z silver or copper/silver electrodes for electrocardiograph, ECG, and 110 at times being a reference electrode). In many implementations, the strip layer 105 may be or may include flex circuitry understood to provide acceptable deformation, twisting, bending and the like, and yet retain robust electrical circuitry connections therewithin. Note, though the electronics 103 and electrodes 108, 109, 110 are shown attached to layer 105; on top for electronics 103, and to the bottom or patient side for electrodes 108, 109, 110; it may be that such elements may be formed in or otherwise disposed within the layer 105, or at least be relatively indistinguishably disposed in relative operational positions in one or more layers with or on or adjacent layer 105 in practice. Similarly, the leads or traces 107 are shown embedded (by dashed line representation in FIG. 1D); however, these may be on the top or bottom side, though more likely top side to insulate from other skin side electrical communications. If initially top side (or bottom), the traces may be subsequently covered with an insulative encapsulant or like protective cover (not separately shown), in many implementations, a flexible material to maintain a flexible alternative for the entire, or majority of layer 105.

On the patient side 102, the ECG electrodes 108, 109 and 110 may be left exposed for substantially direct patient skin contact (though likely with at least a conductive gel applied therebetween); and/or, in many implementations, the patient side electrodes 108, 109 and/or 110 may be covered by a conductive adhesive material as will be described below. The electrodes may be plated with or may be a robust high conductive material, as for example, silver/silver chloride for biocompatibility and high signal quality, and in some implementations may be highly robust and, for one non-limiting example, be adapted to withstand over about 1000 alcohol cleaning cycles between patients. Windows or other communication channels or openings 111, 112 (FIG. 1C) may be provided for a pulse oximeter, for example, for LEDs and a sensor. Such openings 111, 112 would typically be disposed for optimum light communication to and from the patient skin. An alternative disposition of one or more light conduits 111a/112a (and 111b/112b) is shown in a non-limiting example in FIG. 1D more nearly disposed and/or connected to the electronics 103. A variety of alternative placements may be usable herein/herewith.

In some implementations, sampling of the ambient light (with the LEDs off) may be provided, and then subtracting this from each of the pulse-ox signals in order to cancel out the noise caused by sunlight or other ambient light sources.

The LEDs and photodiode sensor may also and/or alternatively be covered with a layer of silicone to remove any air gap between the sensor/LEDs and the patient skin. Two examples of such are set forth in respective FIGS. 1H and 1K; where a silicone layer or covering 121 is shown covering/surrounding the light conduits and/or sensors/LEDs 111c/111d/112c. LED 111c (FIGS. 1H and 1K) might be a Red LED, LED 111d (FIGS. 1H and 1K) might be an IR (infrared) LED and the device 112c (FIGS. 1H and 1K) might be a sensor. This may reduce the light lost to reflection off the skin, and thereby greatly increase the signal and reduce the noise caused by motion of the skin relative to the sensor. In some implementations this silicone might be referred to as a light pipe and in some situations may be clear, colorless, and/or medical grade silicone. As described further below, the silicone layer or covering 121 may also/alternatively be referred to as a light pipe or lens 121/121a/121b herein inasmuch as how it may be involved in light transmitting or to be transmitted therethreough, whether upon emission or received upon reflection or both.

In one or more implementations, a lens 121/121a/121b hereof may be made from a medical grade silicone that is one or more of clear, colorless, soft, low durometer. Exemplars of such specialized silicones that may be used herewith are known as "tacky gels" (several suppliers), and typically have very high-tack adhesives, preferably embedded on both sides. A low durometer silicone combined with double-sided adhesive on the tacky gel allows the construction of a lens 121/121a/121b that may be both conforming to the electronic sensors and skin, as well as, in some implementations, exhibiting properties of motion artifact reduction by limiting movement between the skin-lens-sensor interface. A lens according hereto may also/alternatively be specially shaped such that it can be trapped between layers of the composite adhesive strip (see e.g., alternatives of FIGS. 1D, 1G and 1I and 1J), and in some implementations, with a raised portion the size of the opening, often a rectangular opening, in the adhesive strip that allows the lens to protrude slightly on the patient side of the adhesive strip (see further detail relative to FIG. 1K, described below).

In FIG. 1K an implementation of a further alternative silicone covering or encapsulant 121a for the LEDs and sensor 111c/111d/112c, may include a convex lens at or adjacent the covering external surface 121b. In many implementations, the external surface and lens are one and the same and/or the lens may be defined by the surface 121b of the encapsulant material 121a. What this provides is a structure and method for interfacing pulse oximetry LED emitters 111c/111d and one or more photodiode sensors 112c with the skin surface, whether chest or forehead (e.g., infant or neonate) or otherwise mounted on the patient or user body.

More particularly, as otherwise described herein, a system and/or device 100 hereof may utilize one or multiple LED emitters 111c/111d of selected wavelengths and one or multiple photodiode sensors. However, In order to maximize coupling of the LED/sensor combination to the skin 1001 of a wearer 1000, a lens 121b comprised of optically clear, medical grade silicone may be molded onto or molded such that it may be later attached in covering relationship on the LED/sensor combination 111c/111d/112c. In many implementations, the lens 121b may be partially spherical or perhaps hemispherical in nature, though it need not be. Curvature of other shapes may be useful as well. Curvature reduces loss of skin contact when the device 100 may be moved, whether by wearer motion or otherwise. I.e., motion of the wearer 1000 or the device 100 relative to the wearer 1000 can result in a quasi-rolling contact of the lens on and in relation to the skin 1001. Better maintained skin contact means better data acquisition without interruption and/or with reduced noise.

Moreover, related to the function of maintaining contact is the light piping effect that may be achieved when LEDs and sensors, even of different heights are communicating without air gap interruption through the light pipe of the encapsulant material 121a. With no air gap from emitter to and through the light pipe 121a and with curved surface substantially constant contact with the skin, there is thus no air gap interruption in transmission into and through and reflected back on return from within the skin and back to the sensor via the same light pipe material 121a (transmission and reflection both referring to light travel). This reduces inefficiencies caused by light wave scattering at air gap interfaces (air gaps allow for light to bounce off the skin or other surface). I.e., encapsulation of the LEDs and the sensor; provides no air-gap and a light pipe effect to and the curved surface provides high quality low scattering transmission into the skin and reception of reflection from the skin and bone. The light pipe and curved lens surface maintain uninterrupted contact skin and lens reduces lost signals due skin reflection. The signal to noise ratio goes down and data acquisition goes up in quality.

Such a lens 121b may thus serve one or multiple purposes, including in some instances, inter alia: 1) providing a "light-pipe" effect to assure equal or otherwise high quality coupling of the different height LEDs and sensors, as well as substantially constant coupling to the skin to reduce motion artifact; 2) focusing of emitted light through the skin to the bone; and, 3) focusing of reflected light through the skin to the photodiode sensors.

As a further note, the radius of the lens may be designed to maximize 1) through 3). The height of the lens is designed to allow it to protrude above composite adhesive 113 of the device 100 and into the skin, but not deep enough to disturb the capillary bed which would also result in bad data. Moreover, the radius of curvature and the angles of LED lightwave emission are not necessarily highly controlled and need not be because the LEDs used to penetrate the skin, e.g., the red and infra-red LEDs; provide a very wide array of angles of emission, and thus a large number of reflected array of lightwaves will be focused back to the sensor by a large variety of curved surfaces. I.e., the curved surface is helpful for maintaining contact through movement (accidental or on purpose), and is less important to the angles of transmission through the skin and reflection back to the sensor. In other words, many different radii of curvature will be effective with very little difference in data/wave transmission and reflection; the wide angle emission of LED takes care of what might be a variety of radii. Rather, the curvature may have more limitation in the maintenance of contact due to movement of the device 100—e.g., flatter curvatures won't roll readily, and very small radii of curvature will not transmit or receive as much data.

In some implementations, a radii of curvature found useful have been between about 20 and 40 (both 20.34 mm and 39.94 mm radii of curvature have been found useful) for a device having LEDs and sensors in a compartment of about 12.6 mm by 6.6 mm. It may be noted further that LEDs may be on one side or another or on two opposing sides or perhaps at four or more substantially equi-distant points around a sensor and may provide desirable results.

Note further, pulse oximetry hereof may be with multiple light sources and/or sensors as may be one interpretation of the dispositions of FIGS. 1H and 1K. Typical pulse oximetry circuitry uses one light source (LED) per wavelength (typically red, infrared, and others). However, devices and/or methods hereof may make use of multiple light sources for each wavelength. This allows interrogation of a wider area of capillary bed in/on the patient/wearer in order to reduce the effects of a local motion artifact. Similarly, multiple sensors may be used for the same purpose or advantage.

Furthermore, a combination of driven right leg and/or proxy driven right leg together with pulse oximetry can provide additional benefits. The right leg circuit, proxy right leg and/or driven right leg, whether for chest or forehead or other electrode placement, can remove common mode and power line noise that would/might otherwise be capacitively-coupled into the pulse oximetry sensor and reduce effectiveness thereof. A combination of driven right leg and/or proxy driven right leg and improved pulse oximetry with a lens as described in and for FIG. 1K can significantly reduce such noise, and thereby enhance data acquisition. For driven electrodes see further detail below.

FIG. 1D provides a first example of an adhesive 113 that may be used herewith. The adhesive layer 113 is here a double-sided adhesive for application to the bottom side 102 of the device 100, and a second side, perhaps with a different type of adhesive for adhering to the skin of the human patient (not shown). Different types of materials for adhesion might be used in that the material of choice to which the adhesive layer is to be attached are different; typically, circuit or circuit board material for connection to the device 100, and patient skin (not separately shown) on the patient side. A protective backing 114 may be employed on the patient side until application to the patient is desired. Note, in many applications, the adhesive 113 is anisotropic in that it may preferably be only conductive in a single or substantially a single direction, e.g., the axis perpendicular to the surface of adhesive contact. Thus, good electrically conductive contact for signal communication can be had through such adhesive to/through the adhesive to the electrical contacts or electrodes, 108, 109 and 110. Note, a corresponding one or more light apertures 111b/112b are shown in the adhesive of 113 of the example of FIG. 1D to communicate light therethrough in cooperation with the light conduit(s) 111a/112a in/through layer 105 for communication of light data typically involved in pulse oximetry.

The adhesive may thus be placed or disposed on the device 100, in some implementations substantially permanently, or with some replaceability. In some implementations, the device as shown in FIGS. 1A-1D and/or 1G without (or with in some implementations) the adhesive may be reusable. In many such cases, the adhesive layer 113 may be removed and replaced before each subsequent use, though subsequent re-use of and with a layer 113 is not foreclosed. In a first or subsequent use with a replaceable adhesive layer 113, it may be that the user applying the device to the patient, e.g., the physician or technician or even the patient, him/herself, applies the conductive transfer adhesive 113 to the patient side 102 of the device 100. The protective backing 114 may then be removed, and the device adhered to the patient and activated.

Activation of the device after application to a patient/wearer may occur in a number of ways; in some, it may be pre-set that an affirmative activation interaction may not be necessary from the doctor or patient or like due to either an inertial and/or a pulse oximeter activation which may be substantially automatically activating, e.g., upon receiving sufficient minimum input (movement in case of inertial system or light reflection of blood flow for pulse oximetry); however, a button may be provided at an access 106 or in some other location adjacent the electronics to allow the patient to start or stop the device or otherwise mark an event if desired. In one exemplar implementation the device may be worn for a period such as two weeks for collection of data substantially continuously, or at intervals as may be preferred and established in or by the systems hereof.

After a monitoring period is over, a physician, technician, patient or other person may then remove the device from the patient body, in some instances remove the adhesive, in some instances with alcohol, and may establish a data communication connection for data transfer, e.g., by wireless communication or by insertion/connection of a USB or like data connector to download the data. The data may then be processed and/or interpreted and in many instances, interpreted immediately if desired. A power source on board may include a battery and this can then also be recharged between uses, in some implementations, fully recharged quickly as within about 24 hours, after which the device could then be considered ready for the next patient or next use.

Figure 1G:
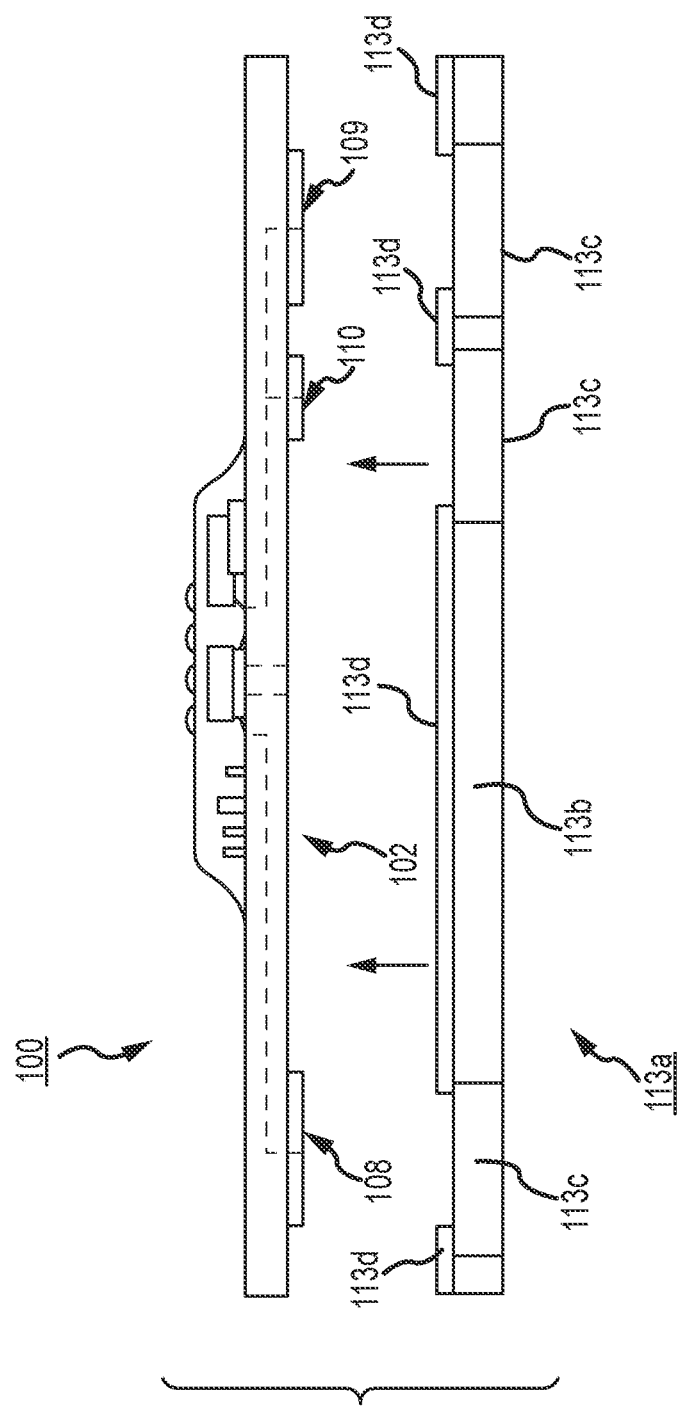
Figure 1I:
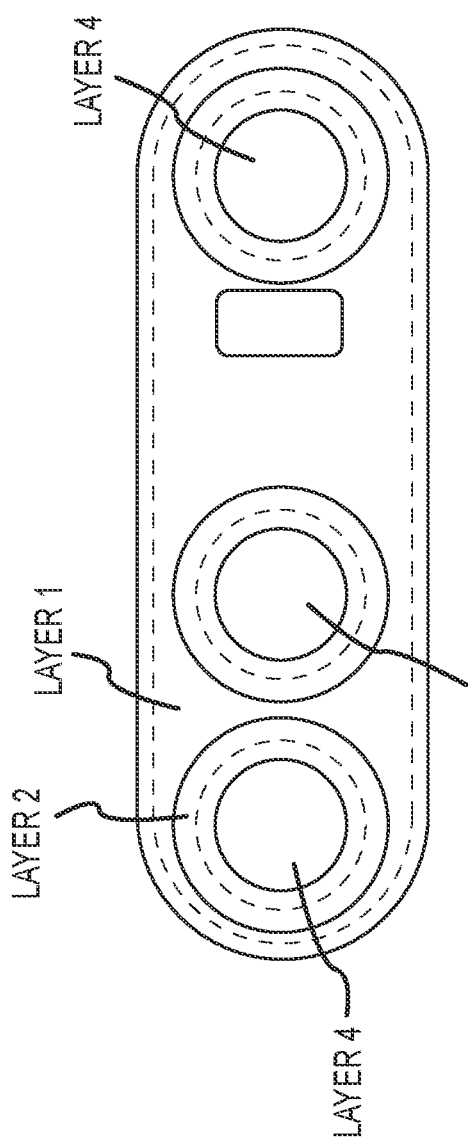
Figure 1J:
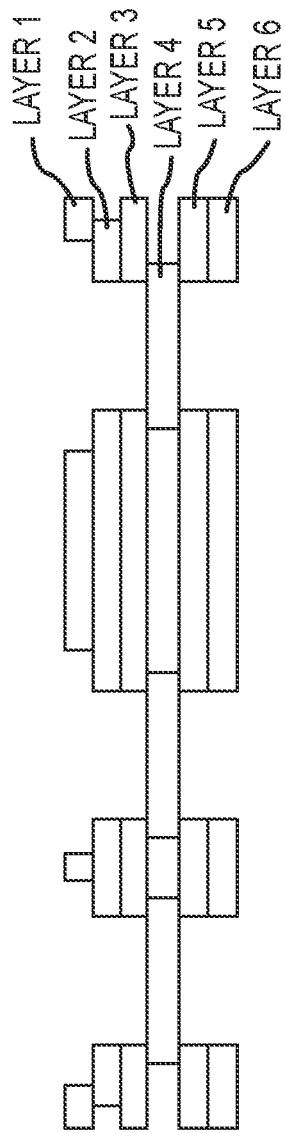

Some alternative conductive adhesives may be used herewith. FIGS. 1E, 1F and 1G show one such alternative conductive adhesive 113a; a bottom plan view in FIG. 1E and elevational side views thereof in FIGS. 1F and 1G (as being connected to a device 100 in FIG. 1G). In some implementations, the conductivity may be anisotropic as introduced above; in some conductive primarily if not entirely in the direction of the Z-Axis; perpendicular to the page (into and/or out of the page) in FIG. 1E, and/or vertically or transversally relative to the long horizontal shown axis of device 100 in the implementation view of FIG. 1F.

The implementation of this particular example includes a composite adhesive 113a which itself may include some non-conductive portion(s) 113b and some one or more conductive portions 113c. The adhesive composite 113a may, as described for adhesive 113 above be double sided such that one side adheres to the patient while the other side would adhere to the underside 102 of the device 100 (see FIG. 1G) so that one or more conductive portions 113c may be disposed or placed in electrically communicative and/or conductive contact with the integrated electrodes on the electronic monitoring device 100. Since the electrodes would operate better where they may be electrically isolated or insulated from each other, yet each making electrical contact or communication with the patient's skin, the adhesive may further be more specifically disposed in some implementations as follows.

As shown in FIGS. 1E and 1F, three isolated conductive portions 113c may be disposed separated from each other by a body portion 113b which may be non-conductive. These could then correspond to the electrodes 108, 109, 110 from the above-described examples, and as more particularly shown schematically in FIG. 1G (note the scale is exaggerated for the adhesive 113a and thus, exact matching to the electrodes of device 100 is not necessarily shown). In some examples, the electrode areas 113c may be a conductive hydrogel that may or may not be adhesive, and in some examples, may be made of a conductive an adhesive conductive material such as 3M Corporation 9880 Hydrogel adhesive (3M Company, St. Paul, Minnesota). These areas 113c may then be isolated from each other by a non-conductive material 113b such as 3M Corporation 9836 tape or 3M double-sided Transfer Adhesive 9917 (3M, St. Paul, MN) or equivalent. The additional layer 113d, if used, might be a 3M 9917 adhesive together with the 113b of a 9836 material. These constructs may provide the effect of creating a low electrical impedance path in the Z-axis direction (perpendicular to page for FIG. 1E and vertically/transversally for FIGS. 1F and 1G) for the electrode areas 113c, and high electrical impedance path between the electrodes in the X/Y directions. (See FIGS. 1E, 1F and 1G; coplanar with the page in FIG. 1E and horizontal and perpendicular to the page in FIGS. 1F and 1G). Thus, a composite adhesive strip can ensure not only device adhering to the patient, but also that the electrodes whether two or as shown three electrodes are conductively connected by conductive portions of the adhesive strip, where the combination of conductive and non-conductive portions can then reduce signal noise and/or enhance noise free characteristics. Electrodes that move relative to skin can introduce noise; that is, electrodes electrically communicative/connected to the skin via a gel may move relative to the skin and thus introduce noise. However, with one or more conductive adhesive portions in a composite adhesive connected to respective electrodes and then substantially securely connected to the skin will keep the respective electrodes substantially fixed relative to the skin and thereby reduce or even eliminate electrode movement relative to the skin. Removal of such movement would then remove noise which would thereby provide a clean signal that can allow for monitoring cardiac P waves which enhances the possibility to detect arrhythmias that couldn't otherwise be detected. Further description is set forth below.

In some implementations, a further optional connective and/or insulative structure 113d may be implemented as shown in FIG. 113d to provide further structural and insulative separation between electrodes with connected to a device 100 on the underside 102 thereof (see FIG. 1G). Though shown separate in FIGS. 1F and 1G, it may be contiguous with the insulative adhesive 113b of these views.

Further alternatives related to the adhesive may be used. In some implementations, a composite adhesive strip may be used having properties to reduce one or more motion artifacts. Typical ECG attachment systems use a conductive gel located over the electrode. Here, however, a hydrogel adhesive may be used which is embedded in a continuous sheet of laminated adhesives that cover the selected regions or the entire footprint of the device. The fact that the hydrogel itself has strong adhesive properties coupled with the complete coverage of the device with adhesives may assure a strong bond between the device and the patient's skin. Contributing to motion artifact reduction may be an alternative vertical placement of the device on the sternum which results in reduced motion artifacts for one or more of ECG signals, photoplethysmography waveforms, and oxygen saturation signals.

In some implementations, composite adhesive improvements may include water-proof encapsulation of the hydrogel adhesive to prevent ohmic impedance reduction resulting in reduction of signal amplitude. This may also help prevent hydrocolloid adhesive degradation. In particular, as shown the non-limitative alternative exemplar in FIGS. 1I and 1J; several layers may be used. Herein, Layer 1 may be a hydrocolloid that is an adhesive designed for long term skin contact by absorbing sweat and cells. Layer 2 may then also be a layer designed for long-term skin contact, however, this layer 2 isolates Layer 3 from contacting the skin. The smaller dimensions of Layer 2 create a gap between Layers 1 and 3. When Layer 1 and 3 bond together, it forms a water-tight seal around Layer 2. This layer, Layer 2, also isolates the Hydrocolloid from the Hydrogel Adhesive, protecting the adhesive properties of the Hydrocolloid. Layers 3 and 5 would then generally be waterproof layers that are electrically isolating, double-sided adhesives. These two layers encapsulate the hydrogel adhesive, preventing a "short circuit" described relative to layer 4 below. Layer 4 is the hydrogel adhesive that is the conductive element hereof. The three islands of hydrogel adhesive of Layer 4 must be kept electrically isolated from each other. However as the hydrocolloid in layer 1 absorbs sweat, it too becomes conductive and creates a potential "short circuit" between the three islands of hydrogel adhesive in Layer 4, reducing signal amplitude. Nevertheless, this "short circuit" may be prevented by layers 3 and 5, described above.

Some alternative implementations hereof may include a driven right leg ECG circuit with one or more chest only electrodes ("Driven Chest Electrode"). In addition to the electrodes used to measure a single or multiple lead electrocardiogram signal, a device 100 may use an additional electrode, as for example the reference electrode 110 (see FIGS. 1A, 1C, 1D and 1G, e.g.) to reduce common mode noise. Such an electrode may function in a manner similar to the commonly-used driven right leg electrode, but may here be located on the patient's chest rather than on the patient's right leg but nevertheless this third/reference electrode may play the role of the leg electrode. This chest electrode may thus mimic a right leg electrode and/or be considered a proxy driven right leg electrode. A circuit, or portion of an overall circuit, adapted to operate in this fashion may include a number of amplifier stages to provide gain, as well as filtering to ensure circuit stability and to shape the overall frequency response. Such a circuit may be biased to control the common mode bias of the electrocardiogram signal. This driven chest electrode implementation may be used in conjunction with a differential or instrumentation amplifier to reduce common mode noise. In this case, the sense electrode may be used as one of the electrocardiogram electrodes. Alternatively, a single-ended electrocardiogram amplifier may be used where the differential electrocardiogram signal is referenced to ground or to some other known voltage.

Figure 2A:
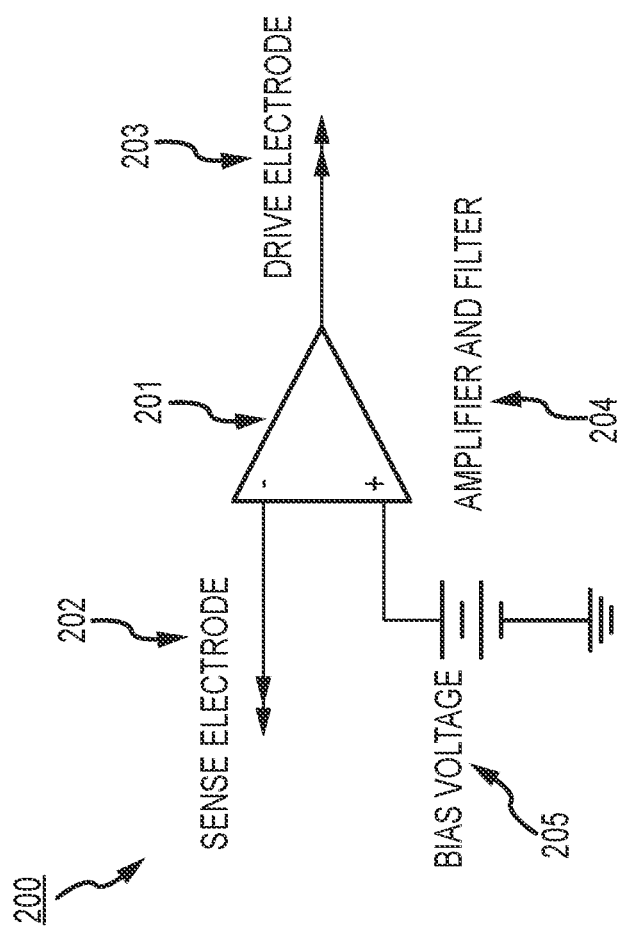
FIG. 2, which includes and is defined by sub-part FIGS. 2A-2D, provides circuit diagrams of alternatives to, in FIGS. 2A-2C, a driven right leg circuit, and in FIG. 2D, pulse oximetry.

A circuit or sub-circuit 200 using a transistor 201 as shown in FIG. 2 may be such a circuit (aka module) and may thus include as further shown in FIG. 2A, a sense electrode 202, a drive electrode 203, and an amplifier 204. Both the sense and drive electrodes 202, 203 are placed on the patient's chest such that they provide an electrical connection to the patient. The amplifier 204 may include gain and filtering. The amplifier output is connected to the drive electrode, the inverting input to the sense electrode, and the non-inverting input to a bias voltage 205. The amplifier maintains the voltage of the sense electrode at a level close to the bias voltage. An electrocardiogram signal may then be measured using additional electrodes. Indeed, as was the case for the improved conductivity through use of anisotropic adhesive portions above, here also or alternatively, the use of this third electrode as a proxy for a right leg electrode (i.e., proxy driven right leg electrode) can provide signal reception otherwise unavailable. Clean signals may thus allow for receiving cardiac P waves which enhances the possibility to detect arrhythmias that couldn't otherwise be detected.

Figure 2C:
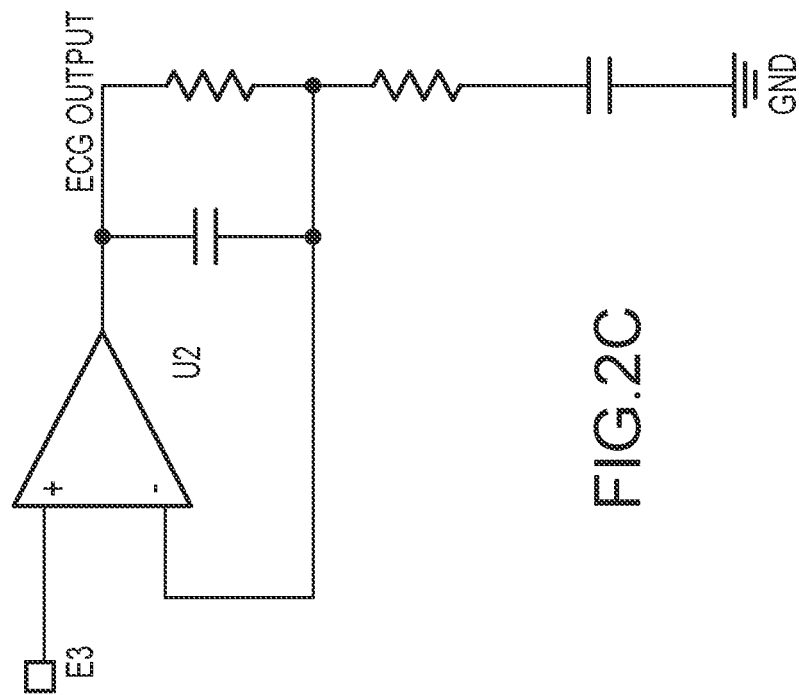
Figure 2B:
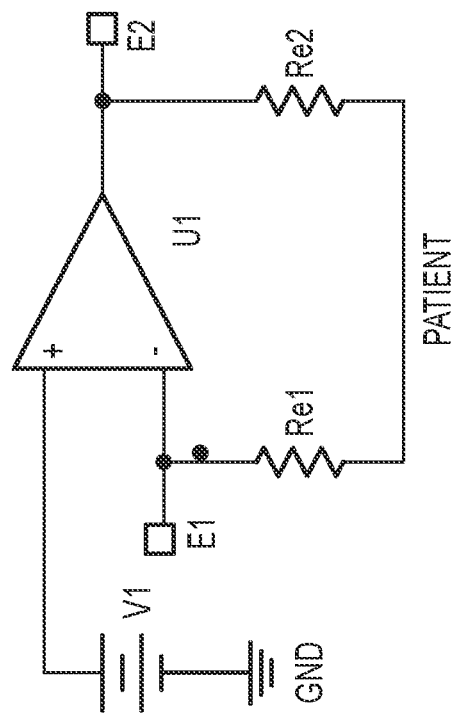

Further alternative descriptions of circuitry include that which is shown in FIGS. 2B and 2C; in which are shown non-limiting alternatives in which three adjacent electrodes E1, E2, and E3 may be used to pick up the ECG signal, one of which electrodes playing the role of the distant limb electrode of traditional ECG monitors. Because the electrode-patient interface has an associated impedance (Re1 and Re2), current flowing through this interface will cause a difference in voltage between the patient and the electrode. The circuit may use a sense electrode (E1) to detect the patient voltage. Because this exemplar circuit node has a high impedance to circuit ground (GND), very little current flows through the electrode interface, so that the voltage drop between the patient and this node is minimized. The first of these alternative, non-limiting circuits (FIG. 2B) also contains an amplifier (U1) whose low-impedance output is connected to a separate drive electrode (E2). The amplifier uses negative feedback to control the drive electrode such that the patient voltage (as measured by the sense electrode E1) is equal to the bias voltage (V1). This may effectively maintain the patient voltage equal to the bias voltage despite any voltage difference between the driven electrode (E2) and the patient. This can include voltage differences caused by power line-induced current flowing between the drive electrode and the patient (through Re2). This arrangement differs from a traditional 'driven-right-leg' circuit in at least two ways: the driven electrode is placed on the patient's chest (rather than the right leg), and the ECG signal is a single-ended (not differential) measurement taken from a third electrode (E3). Because all electrodes are located on the patient's chest in a chest-mounted example, a small device placed there may contain all the necessary electrodes for ECG measurement. One possible benefit of the single-ended measurement is that gain and filtering circuitry (U2 and associated components (FIG. 2C)) necessary to condition the ECG signal prior to recording (ECG Output) requires fewer components and may be less sensitive to component tolerance matching. The examples of FIGS. 2A, 2B and 2C are non-limiting examples and not intended to limit the scope of the claims hereto as other circuits with other circuit elements can be formed by skilled artisans in view hereof and yet remain within the spirit and scope of claims hereof.

In many implementations, a system hereof may include other circuitry operative together with the ECG electrodes, which may thus be accompanied by other sensors to provide time concordant traces of: i) ECG p-, qrs-, and t-waves; ii) O2 Saturation, as measured by Pulse Oxymetry; and/or iii) xyz acceleration, to provide an index of physical activity. Such circuitry may be implemented to one or more of the following electrical specifications. The overall system might in some implementations include as much as two weeks (or more) of continuous run time; gathering data during such time. Some implementations may be adapted to provide as many or even greater than 1000 uses. Alternatives may include operability even after or during exposure to fluids or wetness; in some such examples being water resistant, or waterproof, or watertight, in some cases continuing to be fully operable when fully submerged (in low saline water). Other implementations may include fast data transfer, as for an example where using an HS USB for full data transfer in less than about 90 seconds. A rechargeable battery may typically be used.

A further alternative implementation may include an electronic "ground": In a device hereof, mounted entirely on a flexible circuit board, the ground plane function may be provided by coaxial ground leads adjacent to the signal leads. The main contribution of this type of grounding system may be that it may allow the device the flexibility required to conform and adhere to the skin.

For electrocardiograph; EKG or ECG, some implementations may include greater than about 10 Meg Ohms input impedance; some implementations may operate with a 0.1-48 Hz bandwidth; and some with an approximate 256 Hz Sampling Rate; and may be implementing 12 Bit Resolution. For PPG and Pulse Oximeter, operation may be with 660 and 940 nm Wavelength; about 80-100 SpO2 Range; a 0.05-4.8 Hz Bandwidth; a 16 Hz Sampling Rate; and 12 bit resolution. For an accelerometer: a 3-Axis Measurement may be employed, and in some implementations using a ±2 G Range; with a 16 Hz Sampling Rate; and a 12 Bit Resolution.

For pulse oximetry, an option for PPG ambient light subtraction may be included. A method and circuitry for reducing errors in pulse oximetry caused by ambient light is described and a circuitry option shown in FIG. 2D. Here a correlated double sampling technique is shown for use to remove the effect of ambient light, photo-detector dark current, and flicker noise.

Figure 2D:
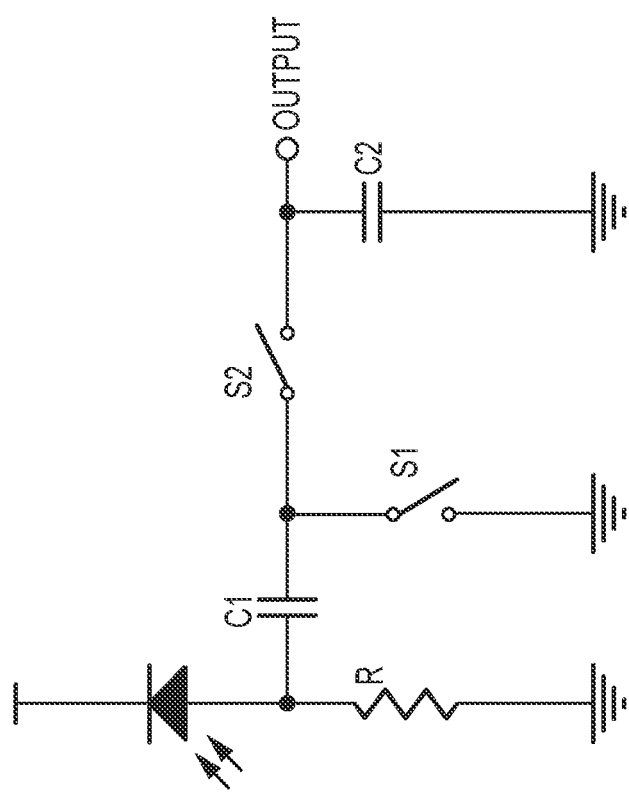

The schematic shown in FIG. 2D may be used where, first, the noise signal may be measured. The light sources are turned off, switch 51 is closed, and switch S2 is open. This allows charge proportional to the noise signal to accumulate on C1. Then switch 51 is opened. At this point the voltage on C1 is equal to the noise signal voltage. Next, the light signal may be measured. The light source is turned on, switch S2 is closed, and charge is allowed to flow through C1 and C2 in series. Then, S2 is opened, and the voltage is held on C2 until the next measurement cycle when the whole process is repeated.

If C1 is much larger than C2, nearly all the voltage will appear on C2, and the voltage on C2 will be equal to the noise-free signal (s). Otherwise, the voltage on C2 will be a linear combination of the previous C2 voltage (p) and the noise-free signal: (C2*s+C1*p)/(C1+C2). This has the effect of applying a first-order, low-pass, IIR discrete-time filter to the signal. If this filtering effect is not desired, the voltage on C2 may be discharged to zero before the signal is measured each cycle, so that the signal held on C2 is simply: (C2*s)/(C1+C2).

This circuit may be used with a trans-impedance amplifier in place of resistor R, a phototransistor in place of the photodiode, and FETs in place of the switches. The output may be followed by additional buffering, amplification, filtering and processing stages.

Figure 3:
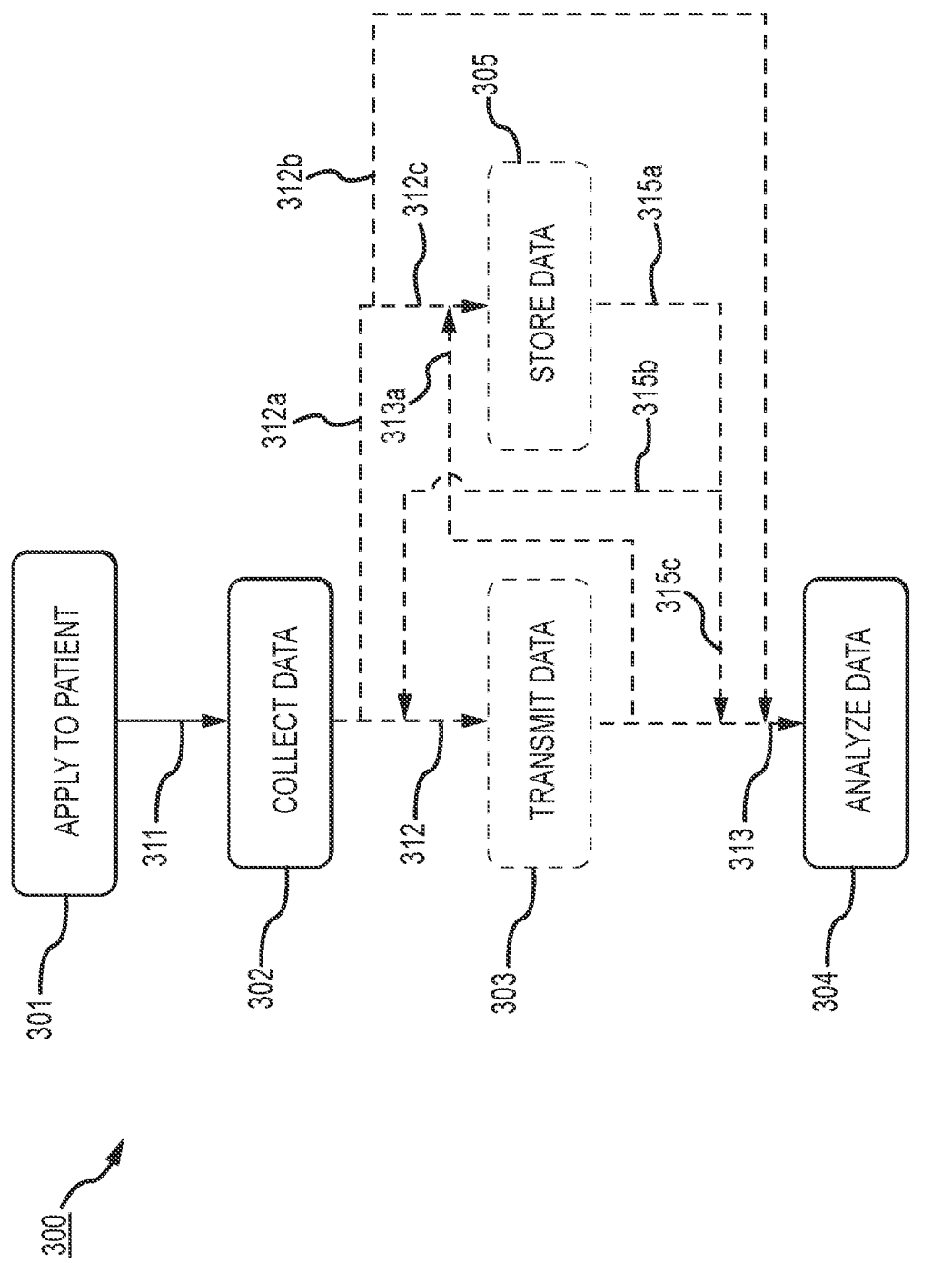
FIG. 3 is a flow chart including alternative methods of use.

Some summary methodologies may now be understood with relation to FIG. 3, though others may be understood through and as parts of the remainder of the disclosure hereof. A flow chart 300 as in FIG. 3 may demonstrate some of the alternatives; where an initial maneuver 301 might be the application of the device 100 to the patient. Indeed, this might include some one or more of the alternatives for adhesive application as described here above, whether by/through use of an adhesive such as that 113 of FIG. 1D, or that of FIGS. 1E, 1F and/or 1G. Then, as shown, in moving by flow line 311, a data collection operation 302 may be implemented. Note, this might include a continuous or substantially continuous collection or an interval or periodic collection or perhaps even a one-time event collection. This may depend upon the type of data to be collected and/or be dependent upon other features or alternatives, as for example whether a long term quantity of data is desired, for ECG for example, or whether for example a relative single data point might be useful, as in some cases of pulse oximetry (sometimes a single saturation point might be of interest, as for example, if clearly too low, though comparison data showing trending over time, may indeed be more typical).

Several alternatives then present in FIG. 3, flow chart 300; a first such might be the following of flowline 312 to the transmission of data operation 303, which could then involve either wireless or wired (e.g., USB or other) data communication from the device 100 to data analysis and/or storage devices and/or systems (not separately shown in FIG. 3; could include computing devices, see e.g., FIG. 4 described below, or the like). Options from this point also appear; however, a first such might include following flow line 313 to the data analysis operation 304 for analyzing the data for determination of the relative health and/or for condition diagnosis of a patient. Computing systems, e.g., a computer (could be of many types, whether hand-held, personal or mainframe or other; see FIG. 4 and description below) could be used for this analysis; however, it could be that sufficient intelligence might be incorporated within the electronics 103 of device 100 such that some analysis might be operable on or within device 100 itself. A non-limiting example, might be a threshold comparison, as for example relative to pulse oximetry where when a low (or in some examples, perhaps a high) threshold level is reached an indicator or alarm might be activated all on/by the electronics 103 of the device 100.

A similar such example, might be considered by the optional alternative flow path 312a which itself branches into parts 312b and 312c. Following flow path 312 a, and then, in a first example path 312b, a skip of the transmit data operation 303 can be understood whereby analysis 304 might be achieved without substantial data transfer. This could explain on board analysis, whether as for example according to the threshold example above, or might in some instances include more detailed analysis depending upon how much intelligence is incorporated on/in the electronics 103. Another view is relative to how much transmission may be involved even if the transmission operation 303 is used; inasmuch as this could include at one level the transmission of data from the patient skin through the conductors 108, 109 and/or 110 through the traces 107 to the electronics 103 for analysis there. In other examples, of course, the transmission may include off-board downloading to other computing resources (e.g., FIG. 4). In some cases, such off-loading of the data may allow or provide for more sophisticated analysis using higher computing power resources.

Further alternatives primarily may involve data storage, both when and where, if used. As with intelligence, it may be that either some or no storage or memory may be made available in/by the electronics 103 on-board device 100. If some storage, whether a little or a lot, is made available on device 100, then, flow path 312a to and through path 312c may be used to achieve some storing of data 305. This may in many cases then, though not necessarily be before transmission or analysis (note, for some types of data multiple paths may be taken simultaneously, in parallel though perhaps not at the same time or serially (e.g., paths 312b and 312c need not be taken totally to the exclusion of the other), so that storage and transmission or storage and analysis may occur without necessarily requiring a completion of any particular operation before beginning or otherwise implementing another). Thus, after (or during) storage 305, flow path 315a may be followed for stored data which may then be transmitted, by path 315b to operation 303, and/or analyzed, by path 315c to operation 304. In such a storage example, which in many cases may also be an on-board storage example, data can be collected then stored in local memory and later off-loaded/transmitted to one or more robust computing resources (e.g., FIG. 4) for analysis. Frequently, this can include long term data collection, e.g., in the manner of days or weeks or even longer, and may thus include remote collection when a patient is away from a doctor's office or other medical facilities. Thus, data can be collected from the patient in the patient's real world circumstances. Then, after collection, the data can be transmitted from its storage on device 100 back to the desired computing resource (FIG. 4, e.g.), and such transmission might be wireless or wired or come combination of both, as for example a blue tooth or Wi-Fi connection to a personal computer (FIG. 4 for one example) which might then communicate the data over the internet to the designated computer for final analysis. Another example might include a USB connection to a computer, either to a PC or a mainframe (FIG. 4), and may be to the patient computer or to the doctor computer for analysis.

If little or no storage or memory is resident on device 100 (or in some examples even where there may be a large amount of resident memory available), then, relatively soon after collection, the data would need to or otherwise might desirably either or both be transmitted and then stored, see path 313a after operation 303, and/or transmitted and analyzed, paths 312 and 313. If path 313a is used, then, more typically, the data storage may be in/on computing resources (not shown in FIG. 3, but see FIG. 4 described below) off-board (though on-board memory could be used as well), and then, any of paths 315a, 315b and 315c may be used.

A feature hereof may include an overall system including one or more devices 100 and computing resources (see FIG.

4, for example) whether on-board device(s) 100, or separate, as for example in personal or mobile or hand-held computing devices (generally by FIG. 4), the overall system then providing the ability for the physician or doctor to have immediate, in-office analysis and presentation of collected test data. This would in some implementations allow for on-site data analysis from the device without utilization of a third party for data extraction and analysis.

Alternative implementations hereof may thus include one or more hardware and software combinations for multiple alternative data source interpretations. As noted above, a device 100 hereof includes hardware that monitors one or more of various physiologic parameters, then generates and stores the associated data representative of the monitored parameters. Then, a system which includes hardware such as device 100 and/or the parts thereof, and software and computing resources (FIG. 4, generally) for the processing thereof. The system then includes not only the collection of data but also interpretation and correlation of the data.

For example, an electrocardiogram trace that reveals a ventricular arrhythmia during intense exercise may be interpreted differently than the same arrhythmia during a period of rest. Blood oxygen saturation levels that vary greatly with movement can indicate conditions that may be more serious than when at rest, inter alia. Many more combinations of the four physiologic parameters are possible, and the ability of software hereof to display and highlight possible problems will greatly aid the physician in diagnosis. Thus, a system as described hereof can provide beneficial data interpretation.

Figure 4:
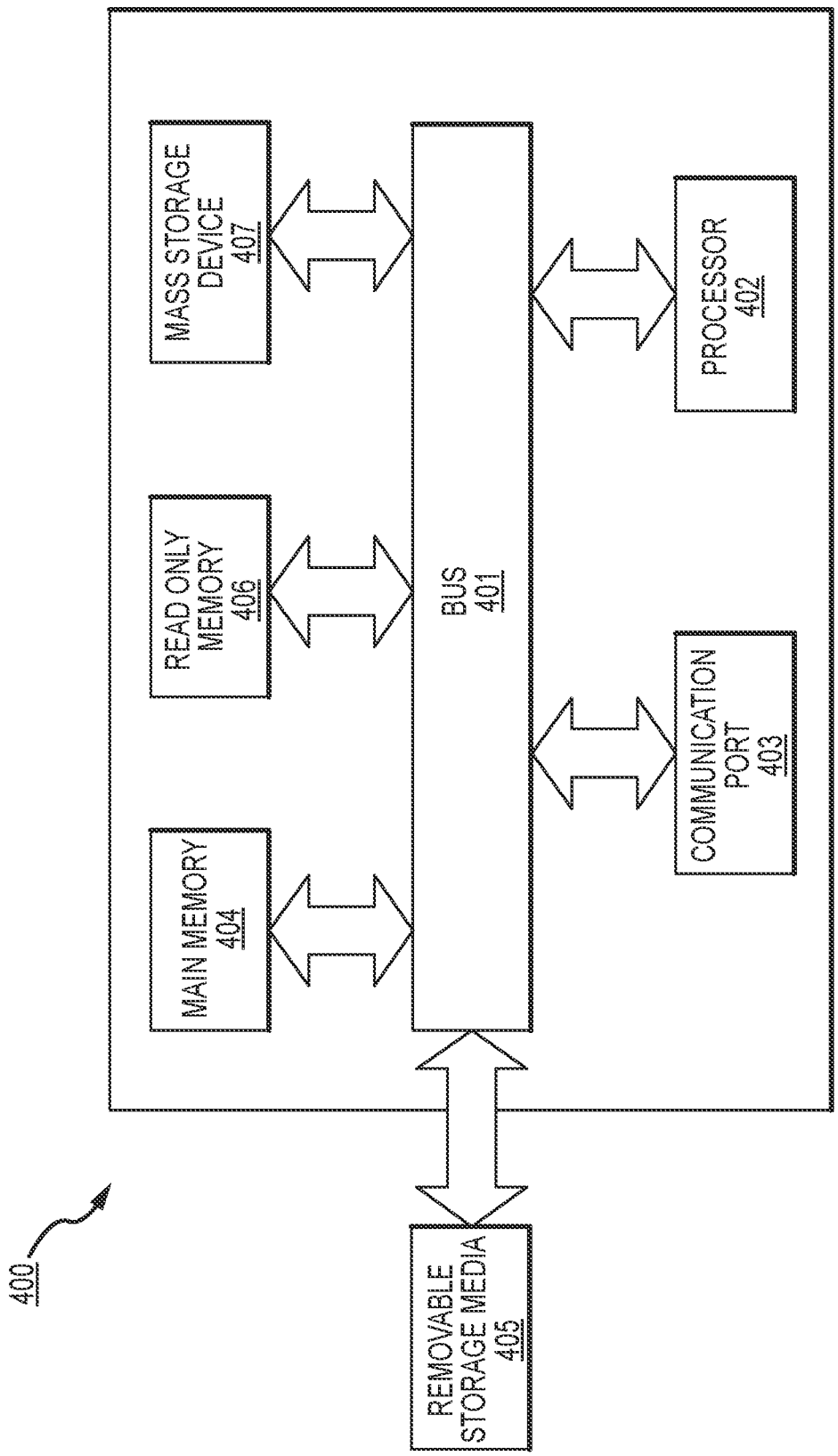
FIG. 4 illustrates an exemplary computer system or computing resources with which implementations hereof may be utilized.

Some of the features which can assist toward this end may be subsumed within one or more of operations 303 and 304 of FIG. 3, wherein data collected on a device 100 can rather simply be communicated/transmitted to computing resources (again, whether on-board device 100 or discrete therefrom as e.g., FIG. 4). For an example, when a patient having had a device applied (operation 301) may return to a physician's office after a test period wherein data was collected (operation 302) the device is connected via one or more data transmission alternatives, as for example, USB to a computer (Windows or Mac) (generally with reference to FIG. 4 and description thereof) in the office, allowing immediate analysis by the physician while the patient waits (note, the device 100 may first have been removed from the patient or might remain thereon pending transmission and analysis for determination of whether more data may be desired). In some implementations, data analysis time may be relatively quick, at approximately 15 minutes in some implementations, and might be achieved with a user-friendly GUI (Graphic User Interface) to guide the physician through the analysis software.

The analysis/software package may be disposed to present the physician with results in a variety of formats. In some implementations, an overview of the test results may be presented, either together with or in lieu of more detailed results. In either case, a summary of detected anomalies and/or patient-triggered events may be provided, either as part of an overview and/or as part of the more detailed presentation. Selecting individual anomalies or patient-triggered events may provide desirable flexibility to allow a physician to view additional detail, including raw data from the ECG and/or from other sensors. The package may also allow data to be printed and saved with annotations in industry-standard EHR formats.

In one implementation, patient data may be analyzed with software having the one or more of the following specifications. Some alternative capabilities may include: 1. Data Acquisition; i.e., loading of data files from device; 2. Data Formatting; i.e., formatting raw data to industry standard file formats (whether, e.g., aECG (xml); DICOM; or SCP-ECG) (note, such data formatting may be a part of Acquisition, Storage or Analysis, or may have translation from one to another (e.g., data might be better stored in a compact format that may need translation or other un-packing to analyze)); 3. Data Storage (whether local, at a clinic/medical facility level or e.g., in the Cloud (optional and allows offline portable browser based presentation/analysis); 4. Analysis which inter alia, may include, e.g., noise filtering (High pass/Low pass digital filtering); and/or QRS (Beat) detection (in some cases, may include Continuous Wave Transform (CWT) for speed and accuracy); and/or 5. Data/Results Presentation, whether including one or more graphical user interface(s) (GUIs) perhaps more particularly with an overall Summary and/or General Statistics and/or Anomaly Summary of Patient triggered event(s); presentation of additional levels of detail whether of Strip view(s) of anomaly data by incident (previous, next) Blood Oxygen saturation, stress correlation or the like; and/or allowing care provider bookmarking/annotations/notes by incident and/or Print capability.

Further, on alternative combinations of hardware with proprietary software packages: I) One on-device software package may be adapted to store the measurements from the data signals acquired from one or more of EKG/ECG (whether right leg and/or p-, qrs- and/or t-waves), or O2 saturation, or xyz acceleration, in a time concordant manner, so that a physician may access a temporal history of the measurements (say, in some examples, over a 1-2 week interval), which would provide useful information on what the patient's activity level was prior to, during, and after the occurrence of a cardiac event. ii) an alternative to alternately manage the real-time transmission of the real-time measured parameters to a nearby station or relay. And/or; iii) an off-device ECG analysis software aimed at recognizing arrhythmias.

The software mentioned above may be industry understood software provided by a 3rd party, or specially adapted for the data developed and transmitted by and/or received from a wearable device 100 hereof. Thorough testing using standard (MIT-BIH/AHA/NST) arrhythmia databases, FDA 510(k) approvals preferred. Such software may be adapted to allow one or more of automated ECG analysis and interpretation by providing callable functions for ECG signal processing, QRS detection and measurement, QRS feature extraction, classification of normal and ventricular ectopic beats, heart rate measurement, measurement of PR and QT intervals, and rhythm interpretation.

In many implementations, the software may be adapted to provide and/or may be made capable of supplying one or more of the following measurements:

Table 1:
1. Heart Rate Min, Max and Average
2. QRS duration average
3. PR interval average
4. QT interval average
5. ST deviation average and, may be adapted to recognize a broad range of arrhythmias such as those set forth here:

Table 2A:
1. SINUS RHYTHM
2. SINUS RHYTHM+IVCD
3. SINUS BRADYCARDIA
4. SINUS BRADYCARDIA+IVCD
5. SINUS TACHYCARDIA

6. PAUSE
7. UNCLASSIFIED RHYTHM
8. ARTIFACT

This first group of 8 given above are arrhythmia types that may be recognizable even if there is no discernible P wave. They are the ones typically recognized by existing products in the outpatient monitoring market that we propose to address.

A second set or group of arrhythmias; below, may require a discernible and measurable P wave. Some implementations hereof may be adapted to be able to detect and recognize them, as device 100 may be able as described above to detect P waves, depending of course, and for example, on whether the strength of the P wave which may be affected by device 100 placement or patient physiology.

Figure 5A:
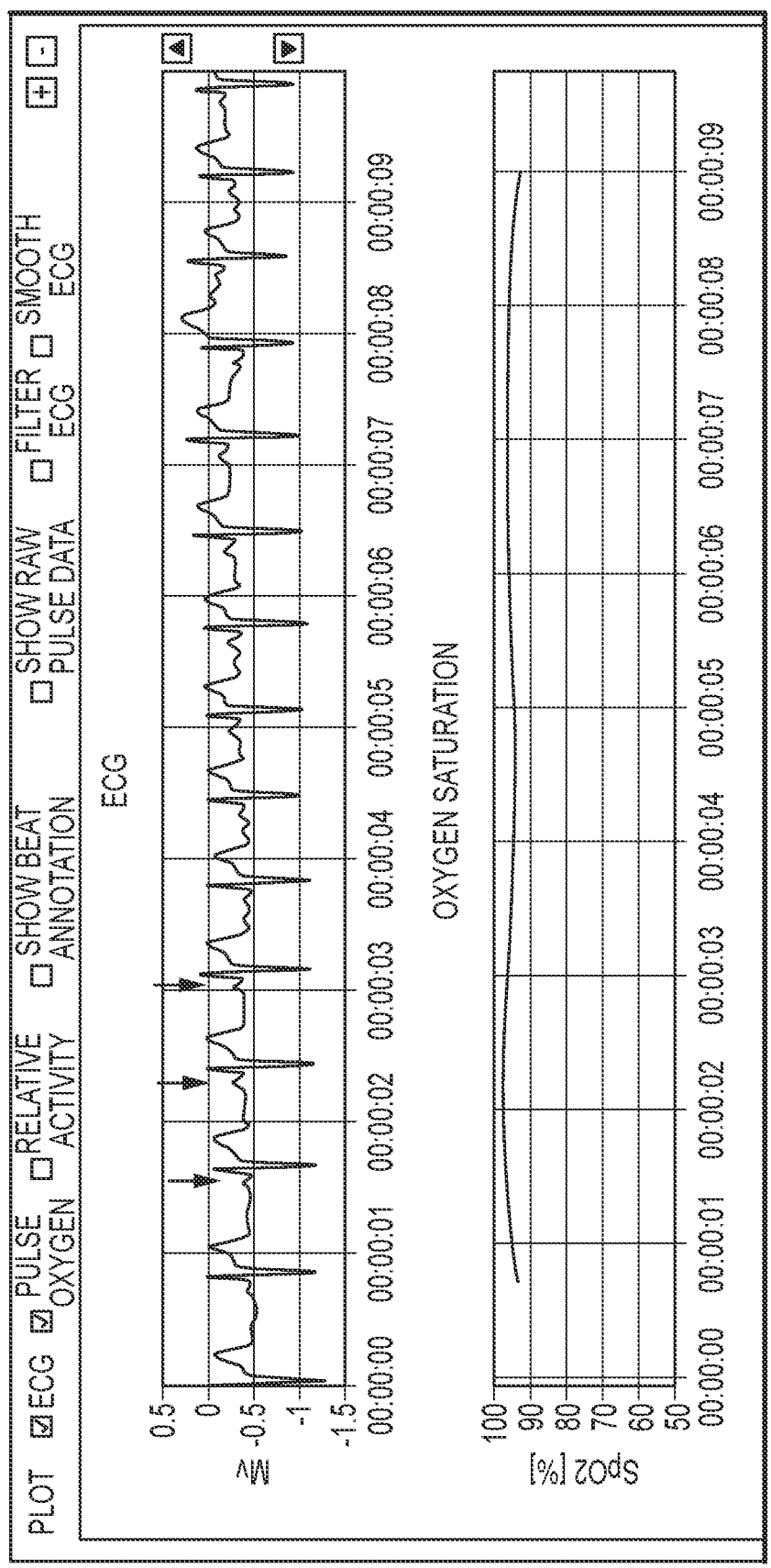
FIG. 5, which includes and is defined by sub-part FIGS. 5A-5D, provides alternative screenshots of alternative software implementations according hereto.

Table 2B:

9. ATRIAL FIBRILLATION/FLUTTER SVR (slow)
10. ATRIAL FIBRILLATION/FLUTTER CVR (normal rate)
11. ATRIAL FIBRILLATION/FLUTTER RVR (rapid
12. FIRST DEGREE AV BLOCK+SINUS RHYTHM
13. FIRST DEGREE AV BLOCK+SINUS TACHYCARDIA
14. FIRST DEGREE AV BLOCK+SINUS BRADYCARDIA
15. SECOND DEGREE AV BLOCK
16. THIRD DEGREE AV BLOCK
17. PREMATURE ATRIAL CONTRACTION
18. SUPRAVENTRICULAR TACHYCARDIA
19. PREMATURE VENTRICULAR CONTRACTION
20. VENTRICULAR COUPLET
21. VENTRICULAR BIGEMINY
22. VENTRICULAR TRIGEMINY
23. IDIOVENTRICULAR RHYTHM
24. VENTRICULAR TACHYCARDIA
25. SLOW VENTRICULAR TACHYCARDIA Further in alternative software implementations; some sample screenshots are shown in FIG. 5. A first such alternative is shown in FIG. 5A, which is an example screenshot showing ECG and Oxygen Saturation data taken by using a patch device such as a device 100 hereof. An extremely clean signal is shown (no filtering or smoothing has been done on this data). Distinct p-waves are also shown (3 of which are shown as an example with arrows). P wave detection can be extremely important for ECG anomaly detection. Oxygen Saturation, as measured by Pulse Oximetry, is shown on the bottom plot. This is data taken by a device on the chest, and is taken in time concordance with the ECG data.

Figure 5B:
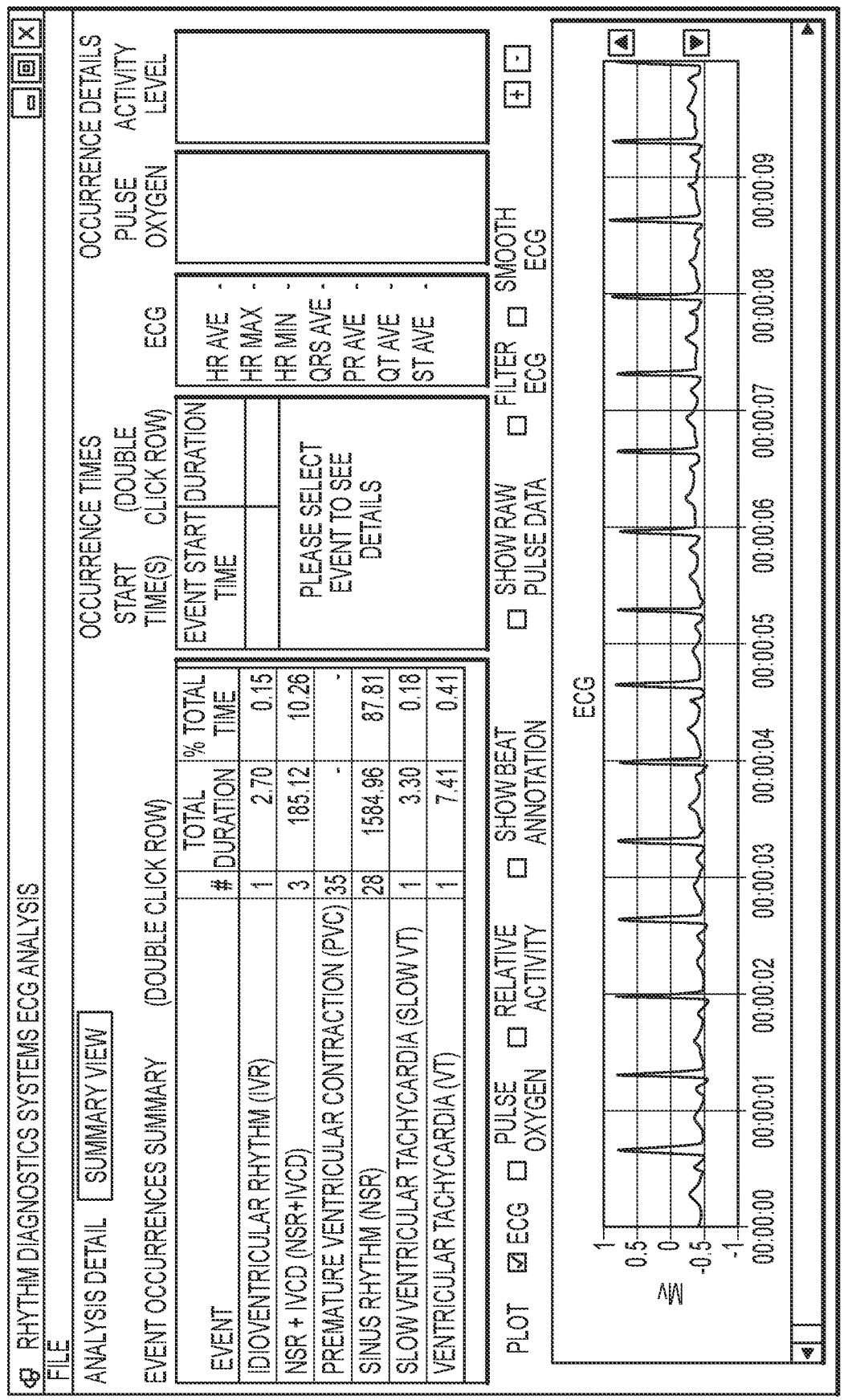

Another alternative is shown in FIG. 5B, which is an example screenshot of Analysis Software. This is a sample of ECG data taken from the MIT-BIH Arrhythmia Database, Record 205. As analyzed by the Analysis system hereof, we see in the Event Occurrences Summary list (top, left) five (5) anomaly types (plus normal sinus rhythm). This list also shows the number of occurrences of each anomaly, total duration of the anomaly in the complete ECG, and the percent time this anomaly occurs in the complete ECG. To view specific instances of each anomaly, the user double clicks the specific row in the Event Occurrences Summary list, as shown in FIG. 5C.

Figure 5C:
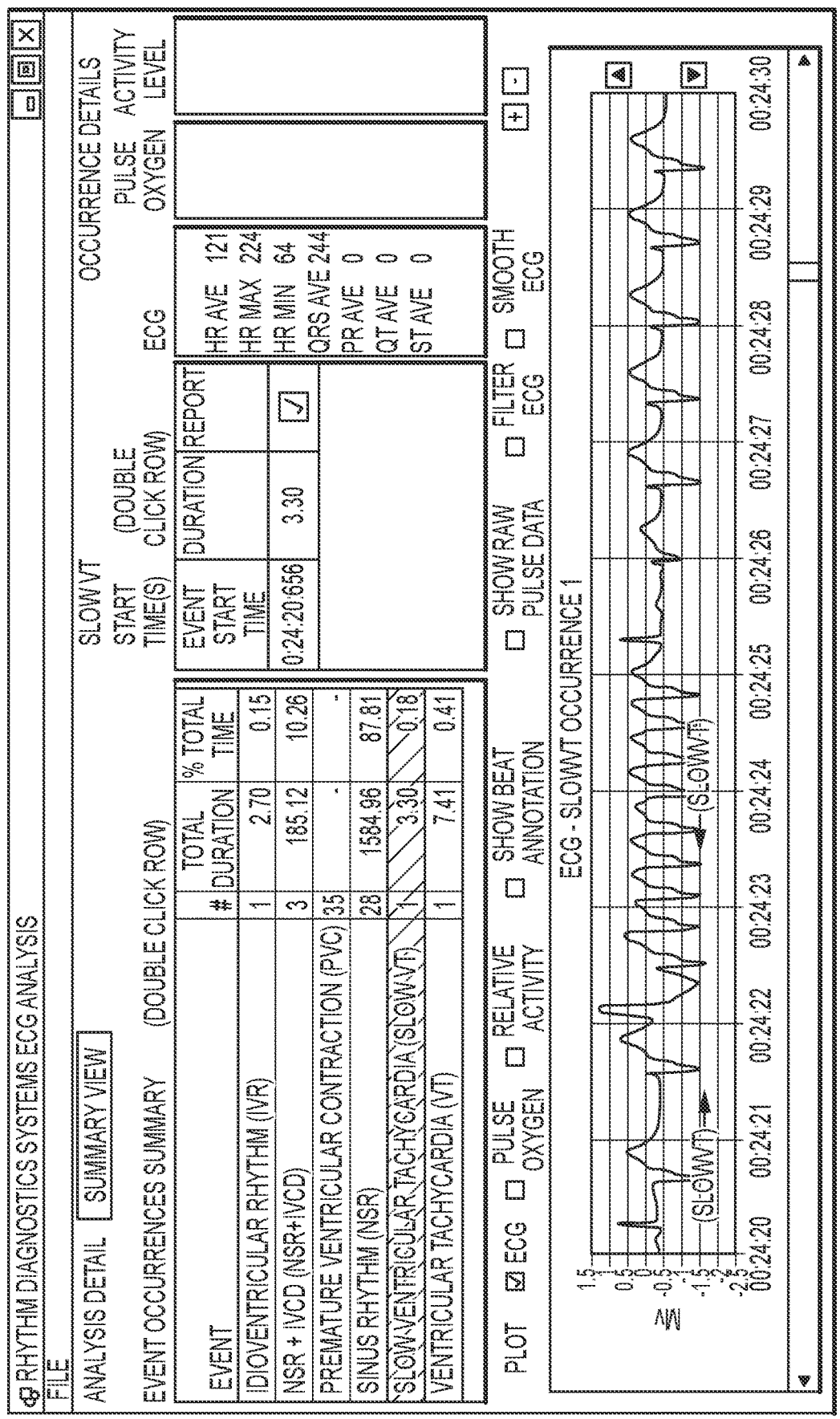

As introduced, FIG. 5C is an example screenshot showing specific instance of Ventricular Tachycardia. The ECG plot automatically navigates to the specific time in the ECG waveform, and marks the beginning and end of the event. More detailed data about this specific event is now shown in the Occurrence Details: HR Average, HR Max, etc. for the duration of this event. To show the instances of another anomaly in this ECT, the user can click on the Premature Ventricular Contraction (PVC) row of the Event Occurrences Summary, as shown FIG. 5D.

Figure 5D:
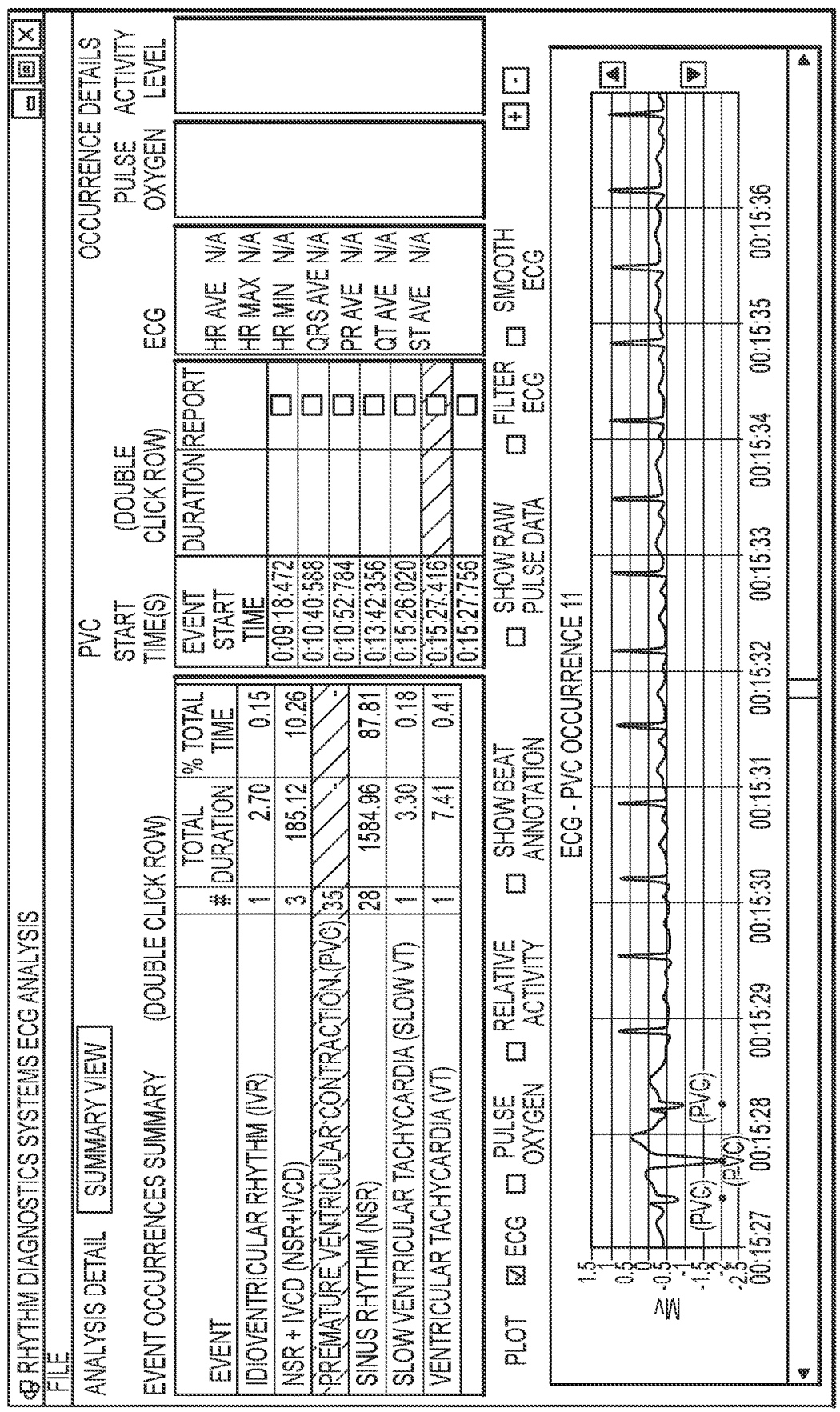

As introduced, FIG. 5D is an example screenshot showing specific instance of Premature Ventricular Contraction. This shows occurrences of the PVC. The Start Times list (middle top) shows all instances of PVC occurrences in this ECG, and lists the start time for each occurrence. In this case, the user can click on the PVC that starts at 00:15:27 (the 11$^{th}$ occurrence). The ECG plot is automatically taken to this point in time to show and indicate the PVC instances in the waveform. Since there are 3 instances of a PVC in this timeslot, all 3 occurrences are marked.

As mentioned above, in one aspect of the developments hereof, ECG signals collected in time concordance with pulse oximetry signals may be used to reduce the noise in the pulse oximetry signals and to permit the calculation of values for oxygen saturation, particularly in circumstances where sensors pulse oximetry data are placed on noise-prone locations of a patient, such as the chest. In some embodiments, this aspect may be implemented by the following steps: (a) measuring an electrocardiogram signal over multiple heart beats; (b) measuring one or more pulse oximetry signals over multiple heart beats such that the electrocardiogram signal and the one or more pulse oximetry signals are in time concordance over one or more heart beats; (c) comparing a portion of the electrocardiogram signal and the one or more pulse oximetry signals in time concordance over one or more heart beats to determine a constant component and a primary periodic component of each of the one or more pulse oximetry signals; and (d) determining oxygen saturation from the constant components and primary periodic components of the one or more pulse oximetry signals. Measurement of the ECG signals and pulse oximetry signals may be implemented by embodiments of devices hereof. In particular, pulse oximetry signals may be a reflective infrared signal and a reflective red light signal collected by a photodetector in a device hereof. Intervals of pulse oximetry signals corresponding to heart beats may be determined by comparing such signals to the time concordant ECG signals. For example (not intended to be limiting), successive R-wave peaks of a time concordant ECG signal may be used to identify such intervals, although other features of the ECG signal may be used as well. Once such intervals are identified, values at corresponding times within the intervals may be averaged to reduce signal noise and to obtain more reliable values for the constant components (sometimes referred to as the "DC components") and the main periodic components (sometimes referred to as the "AC components") of the pulse oximetry signals, e.g. Warner et al, Anesthesiology, 108: 950-958 (2008). The number of signal values recorded in an interval depends on the signal sampling rate of the detectors and processing electronics employed. Also, as the intervals may vary in duration, the averaging may be applied to a subset of values in the intervals. As described below, oxygen saturation values may be computed from such DC and AC components using conventional algorithms. The number of heart beats or intervals over which such averages may be computed may vary widely, as noted below. In some embodiments, signals from one or more heart beats or intervals may be analyzed; in other embodiments, signals from a plurality of heart beats or intervals may be analyzed; and in some embodiments, such plurality may be in the range of from 2 to 25, or in the range of from 5 to 20, or in the range of from 10 to 20.

In further alternative implementations, a linear regression algorithm for Oxygen Saturation may be used. As such, the patient's ECG signal may be used to determine when heart beats occur. The beat locations allow correlated time averaging of each of the two photoplethysmogram signals. A linear regression of the ensemble averages may then be used to determine the linear gain factor between the two signals. This gain factor can be used to determine the patient oxygen saturation.

ECG data may be recorded in time-concordance with two or more photoplethysmographs of different light wavelengths. The heart beats are detected in the ECG signal. These heart beats allow for definition of a 'frame' of photoplethysmogram data for the time between two adjacent heart beats. Two or more of these frames can then be averaged together at each point in time to create an average frame for the time interval. Because the photoplethysmogram is correlated with the heartbeat, the photoplethysmograph signal is reinforced by this averaging. However, any motion artifact or other noise source that is uncorrelated in time with the heartbeat is diminished. Thus, the signal-to-noise ratio of the average frame is typically higher than that of the individual frames.

Having constructed an average frame for at least two photoplethysmographs of different light wavelengths, linear regression can then be used to estimate the gain between the two average frame signals. This gain value may be used to estimate blood oxygen saturation information or other components present in the blood such as hemoglobin, carbon dioxide or others. The process may be repeated for additional light wavelengths in order to do so.

An exemplar/alternative method hereof may include determining the gain between particular signals, as between the red and IR frame signals, if/when such may be used. These may be found by averaging the two frames together first. This may result in a signal with reduced noise. The gain is found by performing linear regression of the red versus combined and IR versus combined and then finding the ratio of these two results.

Another method involves selecting a possible gain value, multiplying the average frame signal by it, and determining the residual error with respect to an average frame of a different wavelength. This process may be repeated for a number of potential gain values. While simple linear regression finds the global minimum gain value, this method allows for finding local minima. Thus, if it is likely that the global minimum represents correlation caused by motion artifact, venous blood movement or another noise source, it may be ignored, and a local minimum may be selected instead.

As mentioned above, patient wearable devices hereof for implementing the above aspects may be particularly useful for monitoring oxygen saturation in noisy regions for such measurements, for example, where there is significant local skin movement, such as the chest location.

Figure 6A:
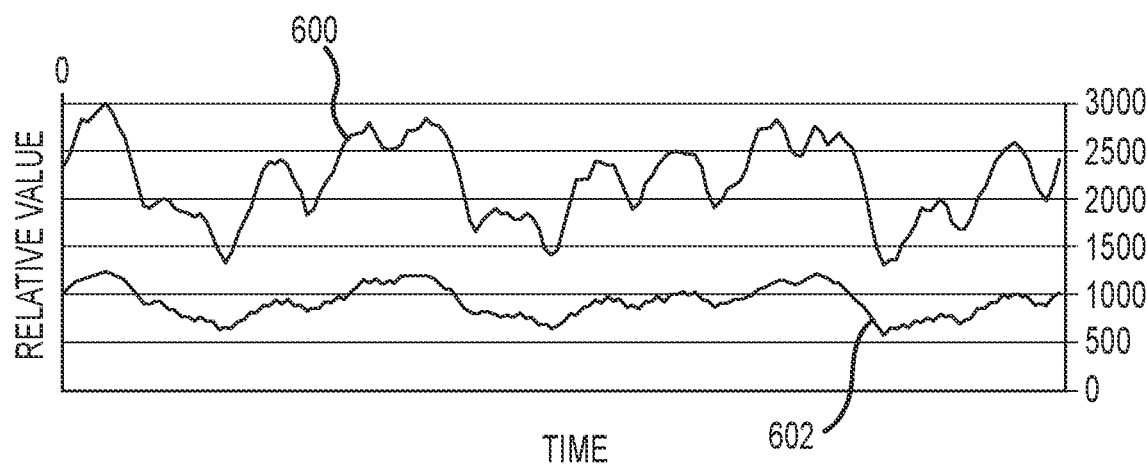
FIGS. 6A and 6B illustrate features of one embodiment for measuring oxygen saturation using pulse oximetry signals and electrocardiogram signals.
Figure 6B:
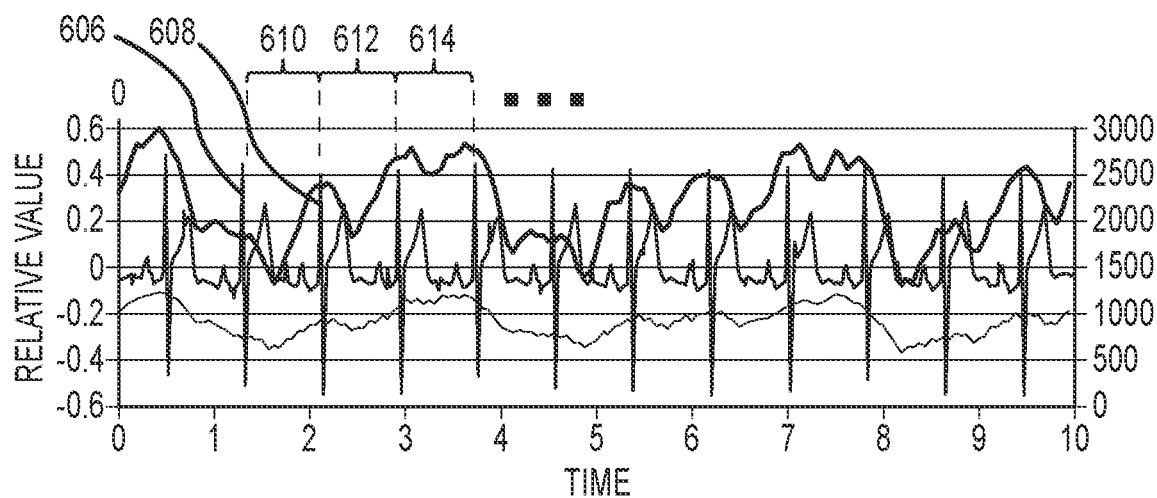
Figure 6C:
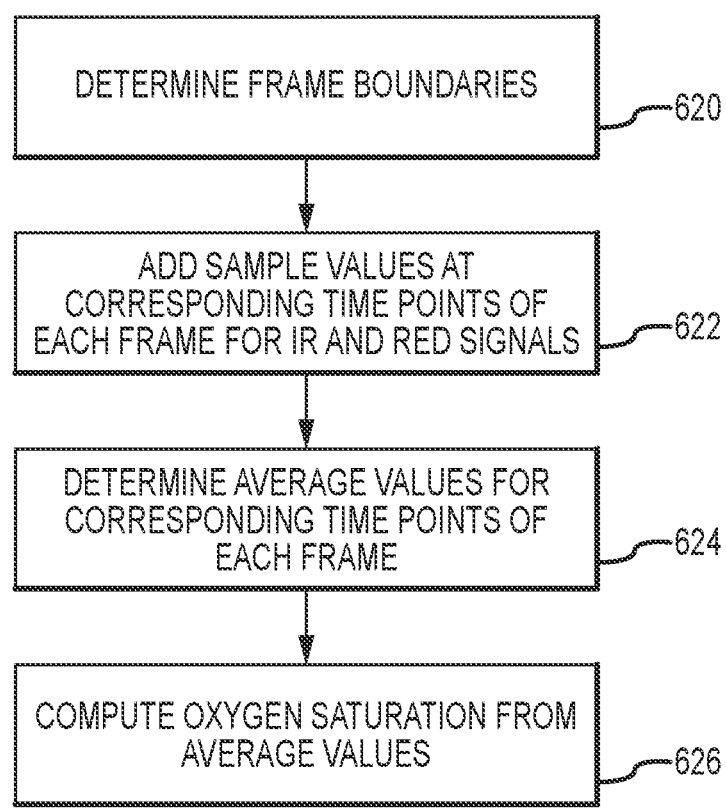
FIG. 6C is a flow chart showing steps of one embodiment for determining oxygen saturation values.

One embodiment of the above aspect hereof is illustrated in FIGS. 6A-6C. In FIG. 6A, curve A (600) illustrates time varying output of the photodiode of a device hereof for infrared (IR) reflection and curve B (602) illustrates time varying output of the photodiode of the device for red light reflection. In some embodiments, the skin is alternatively illuminated by the red and IR LEDs to generate the signals collected by the same photodiode. In FIG. 6B, time synchronized (i.e. time concordant) ECG data, illustrated by curve C (604), is added to the plot of FIG. 6A. Peak values in the ECG data (e.g. peaks 606 and 608) may be used to define frames or intervals of pulse oximetry data. Additional consecutive frames or intervals are indicated by 612 and 614, and further frames may be similarly determined. In accordance with this aspect, pulse oximetry data from a plurality of frames is collected. The magnitude of the plurality may vary widely depending on particular applications. In some embodiments, the plurality of frames collected is from 5 to 25; in one embodiment, a plurality is between 8 and 10 frames. Typically, frames or intervals of pulse oximetry data contain different numbers of signal samples. That is, output from the sensors may be sampled at a predetermined rate, such a 32 samples per second. If the time between ECG peaks varies, then the number of samples per frame will vary. In one embodiment, features in the ECG data serving as the starting points of a frame are selected so that an associated peak in the pulse oximetry data is approximately in the mid-point, or center, of the frame, after which a predetermined number of signal samples are recorded for each frame. Preferably in this embodiment, the predetermined number is selected to be large enough to ensure that the pulse oximetry signal peak is roughly mid-frame. Sample values corresponding to time points above the predetermined value are not used. After a plurality of frames of data is collected, averages of the values at corresponding time points of the frames are computed. The values from such averages AC and DC components of the pulse oximetry data are determined and are then used to compute relative oxygen saturation by conventional methods, such as the ratio-of-ratios algorithm, e.g. Cypress Semiconductor document No. 001-26779 Rev A (Jan. 18, 2010). This basic procedure is summarized in the flow chart of FIG. 6C. Frame size (in terms of number of samples) is determined (620). Values of samples at corresponding time points within each frame are summed (622), after which average values for each time point are computed which, in turn, give the AC and DC components of IR and red light reflection with reduced noise. In some embodiments, values for these components can be used to compute oxygen saturation using conventional algorithms (626). Relative values for oxygen saturation may be converted into absolute values by calibrating the measurements for particular embodiments. Calibration may be carried out in controlled environments where individuals are exposed to varying atmospheric concentrations of oxygen and measured oxygen saturation values are related to corresponding oxygen levels.

In addition to the above embodiment for comparing ECG signals with pulse oximetry signals, a range of other embodiments for such comparing is within the comprehension of those of ordinary skill in the art. For example, in order to find peaks of the AC component of pulse oximetry signals in the presence of noise, features of the time concordant ECG signal that are located at characteristic times preceding and succeeding the pulse oximetry maximum and/or minimum values may be used to reliably determine the pulse oximetry peak and minimum values when averaged over a plurality of heart beats (without the need to average all values of the pulse oximetry signal over the heart beats). For example, if, within an interval, the R wave peak of an ECG signal characteristically preceded a pulse oximetry signal maximum by x milliseconds and trailed a pulse oximetry signal minimum by y milliseconds, then the essential information about the AC component of the pulse oximetry signal may be obtained by repeated measurements of just two values of pulse oximetry signals.

Figure 6D:
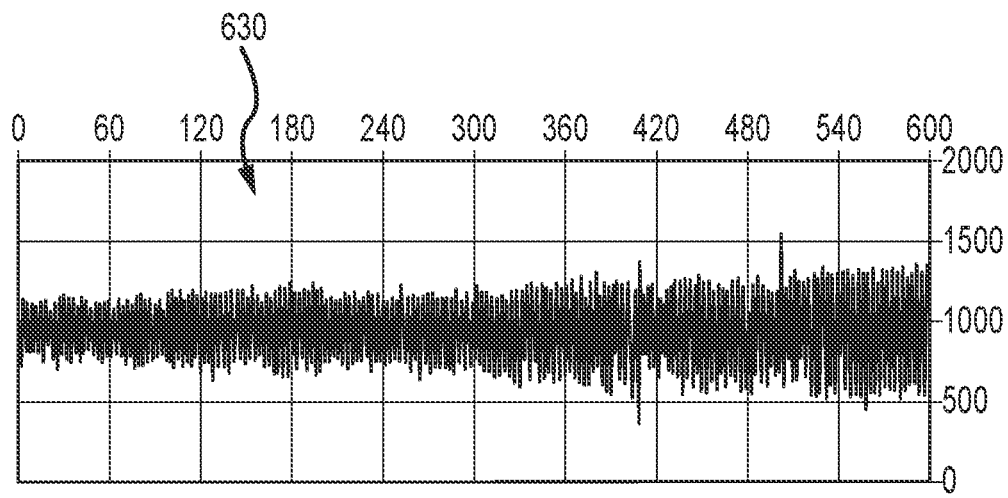
FIGS. 6D and 6E illustrate an embodiment for determining depth of respiration values.
Figure 6E:
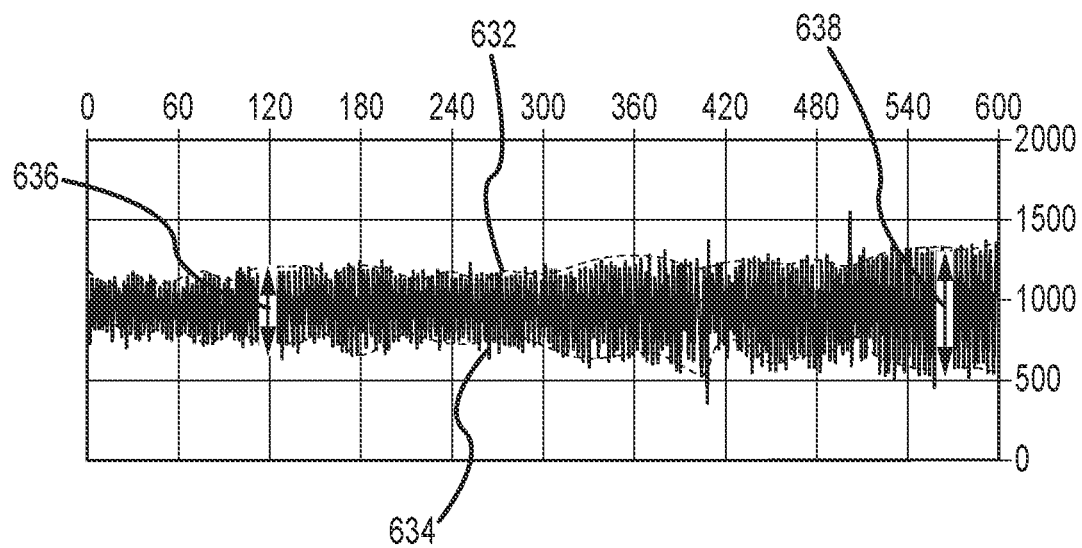

In some embodiments, values for IR or red reflection measured by the photodiode may be used to estimate depth and/or rate of respiration. In FIG. 6D, a curve (630) of Red or IR values over time is illustrated. In FIG. 6E, maximum values and minimum values of curve (630) are shown by dashed curves (632) and (634), respectively. The difference between the maximum and minimum values at a time point is monotonically related to the depth of breath in an individual being monitored. Thus, as illustrated, breaths at time (636) are shallower than those at time (638). In some embodiments, depth of breath versus time may be computed and monitored in an individual. Over time, the rate of respiration can be evaluated from the curve of maximum and minimum values over time.

Moreover, moving from an appreciation of a derivation of a respiration waveform from ECG R-S amplitude and/or R-R intervals, it has been found that a PPG and/or pulse oximeter as described herein can be used to relatively directly estimate a respiration waveform. As the chest expands and contracts during breathing, the motion hereof shows up as a wandering baseline artifact on the PPG signals. The respiration signal may be isolated by filtering out the PPG data to focus on the breathing/respiration signal. This may be particularly so with a chest-mounted PPG.

In addition, a chest mounted accelerometer may also or alternatively be used to measure the respiration waveform, especially when the user is lying on his/her back. As the chest expands and contracts, the chest accelerates up and down (or transversely, or otherwise depending upon orientation), which can be measured by the accelerometer.

Either of these, PPG and/or accelerometer, devices and/or methods may be used discretely or in combination with each other and/or with the above-described ECG-based respiration estimation technique. Using multiple methods may improve accuracy when compared to estimates based on a single method. Respiration rate and depth may then be estimated from the respiration signal using time-domain and/or frequency domain methods.

In some implementations, heart beat timing (e.g., from ECG) and PPG signals can be used to determine pulse transit time; i.e., the time for the pressure wave to travel from the heart to other locations in the body. Measurements of pulse transit time may then be used to determine or estimate blood pressure. Note, the heartbeat timing, ECG and/or PPG signals may be generated by conventional or other to-be-developed methods, systems or devices, or may be developed by wearable devices such as those otherwise described herein. I.e., the algorithms hereof may be separately usable, as well as being usable in the wearable cardiac device.

As disclosed herein elsewhere, the PPG signals of several heart beats may be averaged by correlating each with a respective heartbeat. The result is a PPG frame where the heart rate-correlated PPG signal is reinforced while uncorrelated noise is diminished. Moreover, because the PPG frame is already correlated to the timing of the heartbeat, pulse transit time may be estimated by determining the location of either the peak or minimum with respect to either the beginning or end of the frame itself. This may be done either by finding the minimum and/or maximum sample(s), or by interpolating the signal to find points between measured samples. For example, interpolation may be done with a quadratic fit, a cubic spline, digital filtering, or many other methods.

The pulse transit time may also be estimated by correlating the PPG frame with a sample signal. By shifting the two signals with respect to each other, the time shift resulting in the maximum correlation may be determined. If the sample signal is an approximation of the expected PPG frame, then the time shift with maximum correlation may be used to determine the pulse transit time.

Figure 7A:
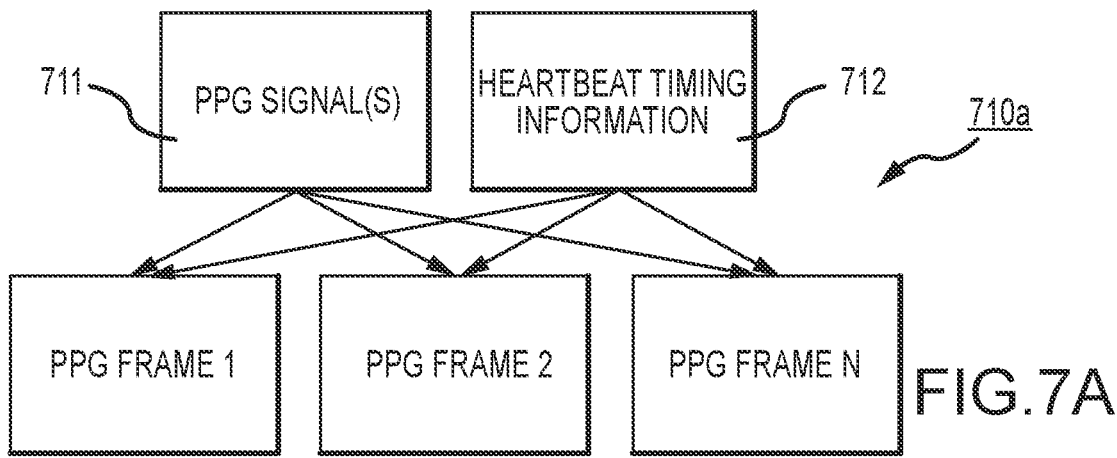
FIGS. 7A, 7B and 7C set forth flow diagrams for alternative methodologies hereof.
Figure 7B:
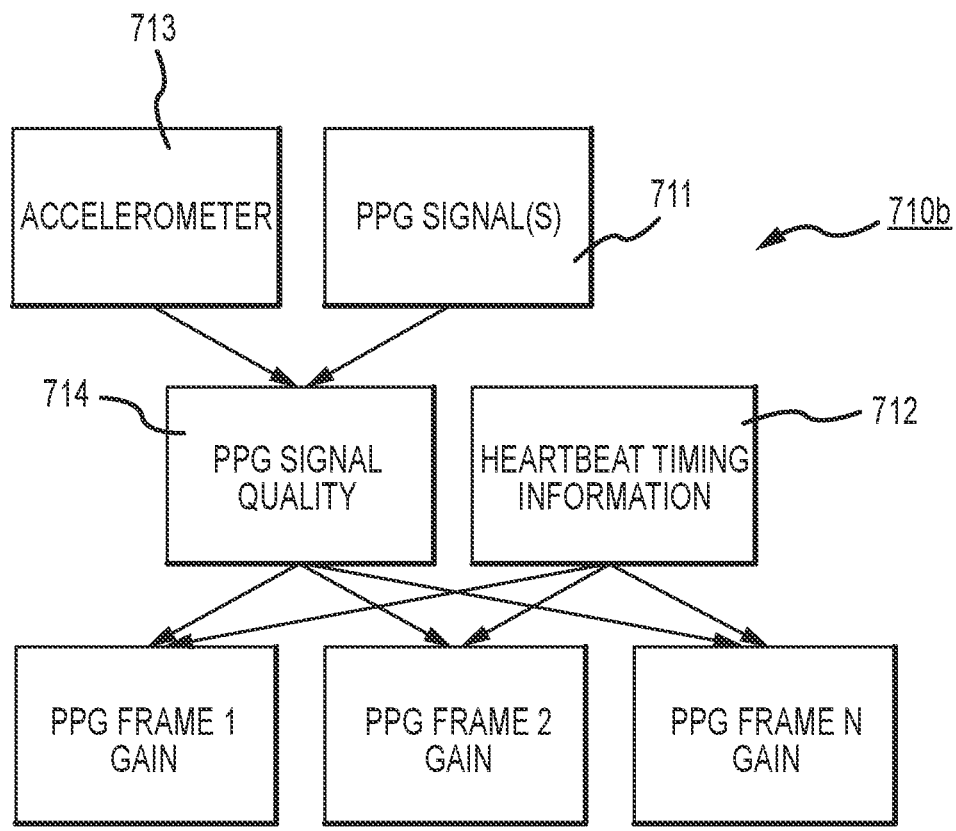
Figure 7C:
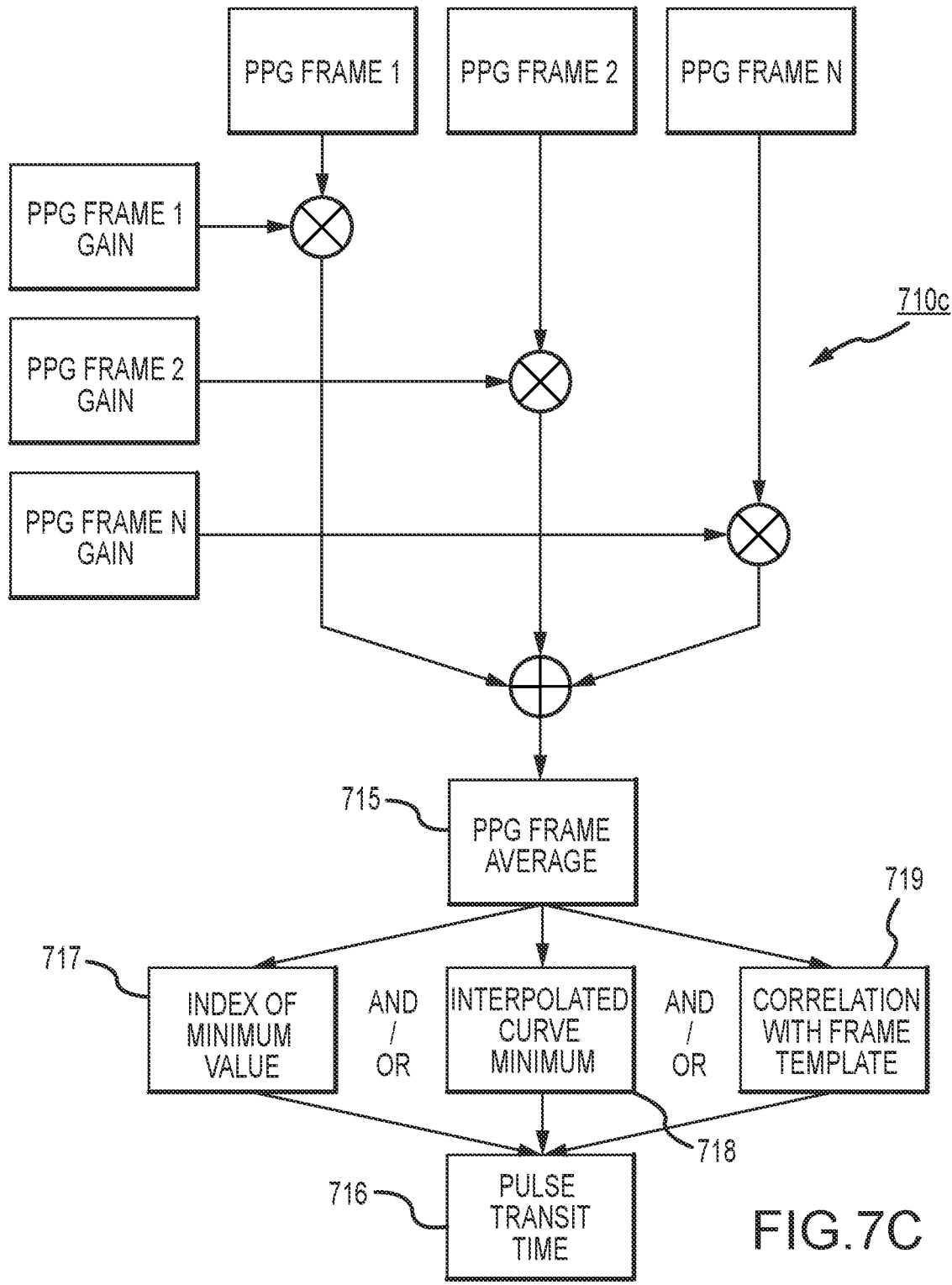

An exemplar methodology or algorithm herefor is described here and shown in the drawing FIGS. 7A, 7B and 7C. Initially, such a method 710 (which includes and/or is defined by parts 710a, 710b and/or 710c) takes at least one heartbeat (typical ECG) signal 712 and at least one PPG signal 711 as input as shown in FIG. 7A, e.g. The heartbeat timing information/signal 712 is used to generate heartbeat timing information by detecting the R-wave or other ECG feature from each beat; multiple ECG signals (i.e. different leads from locations on the body) may be used to obtain a better estimate of the heartbeat timing information. The PPG 711 may use a single light wavelength or signals from multiple light wavelengths. Using the corresponding heartbeat timing information related to each PPG signal 711, each PPG signal 711 is segmented into "frames," see PPG Frame 1, PPG Frame 2 and PPG Frame N in FIG. 7A, where each frame contains the PPG signal of a single wavelength for the duration of one corresponding beat of the heart.

Optionally, but, typically, a PPG signal quality estimate may also be performed. An example of this is shown as method part 710b in FIG. 7B. This estimate may consider the variance of the PPG signal, the estimated signal-to-noise ratio of the PPG signal, PPG signal saturation, patient motion information from an accelerometer or gyroscope, an ECG or impedance measurement noise estimate, or other information about the PPG signal quality. Shown in FIG. 7B is an exemplar using accelerometer signal 713 in conjunction with PPG signal 711 to generate a PPG Signal Quality Value/Estimate 714. This signal quality estimate 714 may then be used in conjunction with the heartbeat timing information 712 to generate the gain for each frame, see PPG Frame 1 Gain, PPG Frame 2 Gain and PPG Frame N Gain in FIG. 7B, where lower signal quality results in a lower gain. To reduce computation time, the signal quality estimate 714 may be omitted and a constant may be used for the gain information.

As shown in FIG. 7C, the gain information (PPG Frame 1 Gain, PPG Frame 2 Gain and PPG Frame N Gain from FIG. 7B) may be used (here shown as combined/manipulated) with the frame information (PPG Frame 1, PPG Frame 2 and PPG Frame N from FIG. 7A) to create a weighted, n-sample moving-average frame 715, where the PPG signal that is correlated with the heartbeat timing is reinforced while the uncorrelated noise is reduced. The number of samples included in the frame (n) 715 may be adapted to reduce noise or decrease response time. The frames may be additionally weighted by time in order to increase the contribution of recent or near-future frames with respect to frames that are further away and potentially less-relevant. This additional weighting by time may be implemented using an IIR or FIR filter.

Once the average frame 715 has been produced for a given instant in time, the pulse transit time 716 may be determined by finding the shift in the frame signal with respect to the heartbeat. This may be done simply by finding the sample index 717 where the signal is at a minimum or maximum and comparing it with the frame boundary (heartbeat timing) to determine the pulse transit time. For a more precise result, the signal may be interpolated 718 using a spline or polynomial fit around the minimum or maximum values, allowing the minimum or maximum to be determined with greater precision than the sample rate. Finally, the frame may be compared 719 to a reference frame template, where the average frame is shifted with respect to the template. The shift with the highest correlation between the average frame and the template indicates the transit time 716. This reference template may be a predetermined signal, or it may be allowed to adapt by using a long-term frame average with a known transit time.

Note, such methodologies may be used with PPG and heartbeat timing information obtained from a variety of sources, including but not limited to conventional and/or to-be-developed technologies; or, may be obtained one or the other alone or together and/or together with quality signal (PPG variance, estimated PPG signal-to-noise ratio, PPG signal saturation, patient motion accelerometer or gyroscope data, an ECG or impedance measurement noise estimate, or other information about the PPG signal quality) obtained from a wearable device and/or system as described further hereinbelow.

Some further alternatives may include data transmission and/or interpretation by local medical facilities, whether physician or doctor offices or e.g., ICU/CCU (Intensive Care/Coronary Care Units). Accordingly, a device 100 hereof that will measure one or more of a variety of physiologic signals, possibly including electrocardiogram, photoplethysmogram, pulse oximetry and/or patient acceleration signals will be placed on the patient's chest and held with an adhesive as described herein. The device transmits the physiologic signals wirelessly or by wire (e.g., USB) to a nearby base station for interpretation and further transmission, if desired. The wireless transmission may use Bluetooth, Wi-Fi, Infrared, RFID (Radio Frequency IDentification) or another wireless protocol. The device may be powered by wireless induction, battery, or a combination of the two. The device 100 monitors physiological signals and/or collects data representative thereof. The collected data may then be transmitted wirelessly or by wire connection, in real time, to the nearby base station. The device may be wirelessly powered by the base station or by battery, removing the need for wires between the patient and the station.

Relatedly and/or alternatively, patients or wearers may be monitored wirelessly in a hospital, including an ICU (Intensive Care Unit) or other facility. As such, an ECG signal may be measured on a patient using a small, wireless patch device hereof. The signal is then digitized and transmitted wirelessly to a receiver. The receiver converts the signal back to analog, such that it approximates the original ECG signal in amplitude. This output is then presented to an existing hospital ECG monitor through the standard electrode leads. This allows the patient to be monitored using existing hospital infrastructure without any lead wires necessarily connecting the patient to the monitor. Patient chest impedance may be measured as well, allowing the reconstructed signal to approximate the ECG signal not only in amplitude, but in output impedance as well. This can be used to detect a disconnected patch. The output impedance may be continuously variable, or it may have discrete values that may be selected (e.g. one low value for a connected device and one high value to signify the patch has come loose). The impedance may also be used to signify problems with the wireless transmission.

Other alternative implementations may include coupling one or multiple sensors mounted to the forehead of an infant. Initially, a method of obtaining oxygen saturation data by mounting a device in the forehead of an infant might be used as introduced. However, an expansion or alternative may include coupling oxygen saturation sensors with relative position and temperature sensors on the same forehead-mounted device. The combined data can be utilized to ascertain if an infant is in any danger of suffocation due to a face-down position.

Thus, some of the alternative combinations hereof may include one or more of: 1) medical grade adhesives (from many possible sources) selected for their ability to maintain in intimate contact with the skin without damaging it, for several days (up to, say 10 days or two weeks in some examples), as well as operability with different types of sensors; 2) conductive electrodes or photo-sensitive detectors able to supply electrical signals from the skin or from the photo-response of cutaneous or subcutaneous tissues to photo-excitation; 3) amplifiers, microprocessors and memories, capable of treating these signals and storing them; 4) power supply for the electronics hereof with stored or with wirelessly accessible re-chargeability; 5) flex circuits capable of tying the above elements together within a flexible strip capable of conforming to a cutaneous region of interest.

Examples of physiological parameters that may be subject to monitoring, recordation/collection and/or analyzing may include one or more of: electrocardiograms, photo responses of photo-excited tissues for e.g., oxygen saturation of blood; pulse rates and associated fluctuations; indications of physical activity/acceleration. One or more of these may be used in monitoring ambulatory cardiac outpatients over several days and nights, which could thereby provide for recording, for post-test analysis, several days' worth of continuous ECG signals together with simultaneous recording of O2 saturation and an index of physical exertion. Similarly, one or more of these may be used in monitoring ambulatory pulmonary outpatients over several days and nights for recording, for post-test analysis, O2 saturation together with simultaneous recording of an index of physical activity. Alternatively and/or additionally, one or more of these could be used for monitoring in-patients or other patients of interest, as for example neonates, wirelessly (or in some cases wired), whether in clinics, emergency rooms, or ICUs, in some instances detecting the parameters of EKG, O2 and/or physical exertion, but instead of storing them would transmit them wirelessly to either a bedside monitor or a central station monitor, thus freeing the patient from attachment to physical wires. In particular, devices hereof may be adhered to the forehead of a neonate for monitoring respiration and oxygen saturation. In further alternatives, devices hereof may be used to monitor respiration and ECG of patients suffering from sleep apnea.

An exemplary computer system or computing resources which may be used herewith will now be described, though it should be noted that many alternatives in computing systems and resources may be available and operable within the reasonably foreseeable scope hereof so that the following is intended in no way to be limiting of the myriad possible computational alternatives properly intended within both the spirit and scope hereof.

Some of the implementations of the present developments include various steps. A variety of these steps may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware. As such, FIG. 4 is an example of computing resources or a computer system 400 with which implementations hereof may be utilized. According to the present example, a sample such computer system 400 may include a bus 401, at least one processor 402, at least one communication port 403, a main memory 404, a removable storage media 405, a read only memory 406, and a mass storage 407. More or fewer of these elements may be used in a particular implementation hereof.

Processor(s) 402 can be any known processor, such as, but not limited to, an Intel® Itanium® or Itanium 2® processor(s), or AMD® Opteron® or Athlon MP® processor(s), or Motorola® lines of processors. Communication port(s) 403 can be any of an RS-232 port for use with a modem based dialup connection, a 10/100 Ethernet port, a Universal Serial Bus (USB) port, or a Gigabit port using copper or fiber. Communication port(s) 403 may be chosen depending on a network such a Local Area Network (LAN), Wide Area Network (WAN), or any network to which the computer system 400 connects or may be adapted to connect.

Main memory 404 can be Random Access Memory (RAM), or any other dynamic storage device(s) commonly known in the art. Read only memory 406 can be any static storage device(s) such as Programmable Read Only Memory (PROM) chips for storing static information such as instructions for processor 402.

Mass storage 407 can be used to store information and instructions. For example, hard disks such as the Adaptec® family of SCSI drives, an optical disc, an array of disks such as RAID, such as the Adaptec family of RAID drives, or any other mass storage devices may be used.

Bus 401 communicatively couples processor(s) 402 with the other memory, storage and communication blocks. Bus 401 can be a PCI/PCI-X or SCSI based system bus depending on the storage devices used.

Removable storage media 405 can be any kind of external hard-drives, floppy drives, IOMEGA® Zip Drives, Compact Disc-Read Only Memory (CD-ROM), Compact Disc-Re-Writable (CD-RW), Digital Video Dis-Read Only Memory (DVD-ROM).

The components described above are meant to exemplify some types of possibilities. In no way should the aforementioned examples limit the scope of the invention, as they are only exemplary embodiments.

Embodiments of the present invention relate to devices, systems, methods, media, and arrangements for monitoring and processing cardiac parameters and data, inter alia. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A device for monitoring a physiological parameter, the device being configured to be adhered to the skin of a subject for the physiological parameter monitoring; the device comprising:
a substrate;
a conductive sensor connected to the substrate, and
an adhesive having:
at least one conductive adhesive portion, and
at least one non-conductive adhesive portion;
the at least one conductive adhesive portion and the at least one non-conductive adhesive portion disposed in contact with each other;
and the adhesive being defined as:
double-sided defining adhesive on two sides of the adhesive,
the adhesive defining the at least one conductive adhesive portion and the at least one non-conductive portion as an element formed together as an adhesive apart from the substrate and the conductive sensor;
the double-sided adhesive being attached to the substrate and the conductive sensor;
the at least one conductive adhesive portion being disposed in conductive communicative contact with the conductive sensor, and
being configured to be conductively adhered to the skin of the subject for conductive signal communication from the subject to the conductive sensor.

2. A device according to claim 1 the conductive adhesive portion of the adhesive is connected to the conductive sensor and configured to be substantially securely connected to the skin to maintain the conductive sensor substantially fixed relative to the skin and thereby one or both reduces or eliminates possible sensor movement relative to the skin.

3. A device according to claim 2 wherein the connection of the conductive adhesive portion to the conductive sensor and to the skin is configured to substantially remove movement of the conductive sensor relative to the skin to one or both reduce noise or provide a clean signal.

4. A device according to claim 1 wherein the physiological parameter includes one or more signals for one or more or all of electrocardiography, photoplethysmography, pulse oximetry, temperature, or subject acceleration.

5. A device according to claim 4 wherein the conductive sensor is an electrode for electrocardiography.

6. A device according to claim 1 the at least one conductive adhesive portion of the adhesive being embedded within the at least one non-conductive adhesive portion in a single layer.

7. A device according to claim 1 comprising
a plurality of conductive sensors connected to the substrate,
the adhesive having a plurality of conductive adhesive portions,
the plurality of conductive adhesive portions being disposed in conductive communicative contact with respective ones of the plurality of conductive sensors, and being adapted to be conductively adhered to the skin of the subject for conductive signal communication from the subject to the conductive sensor.

8. A device according to claim 7 wherein the plurality of conductive sensors include at least one, two or three electrodes for electrocardiography.

9. A device according to claim 1 the device being configured to be disposed on the torso.

10. A device for monitoring a physiological parameter, the device being configured to be adhered to the skin of a subject for the physiological parameter monitoring; the device comprising:
a substrate;
a conductive sensor connected to the substrate, and
an adhesive having:
at least one conductive hydrogel adhesive portion, and
at least one continuous sheet portion;
the at least one conductive hydrogel adhesive portion and the at least one continuous sheet portion disposed in contact with each other, the at least one conductive hydrogel adhesive portion embedded within the at least one continuous sheet portion;
and the adhesive being defined as:
double-sided defining adhesive on two sides of the adhesive,
the adhesive defining the at least one conductive hydrogel adhesive portion and the at least one continuous sheet portion as an element formed together as an adhesive apart from the substrate and the conductive sensor;

the conductive hydrogel adhesive portion being embedded within the continuous sheet portion and being attached to the substrate and the conductive sensor;

the at least one conductive hydrogel adhesive portion being disposed in conductive communicative contact with the conductive sensor and being configured to be conductively adhered to the skin of the subject for conductive signal communication from the subject to the conductive sensor.

11. A device according to claim 10 the conductive hydrogel adhesive portion of the adhesive being embedded within the continuous sheet portion.

12. A device according to claim 11 the connection of the conductive hydrogel adhesive portion is a central layer, and a hydrocolloid is disposed thereon as at least one other layers.

13. A device according to claim 10 the device being configured to be disposed on the torso.

14. A device according to claim 10 wherein the device is vertically placed on the sternum.

15. A device according to claim 10 which provides reduced motion artifacts for one or more of ECG signals, photoplethysmography waveforms, and oxygen saturation signals.

16. A device according to claim 10 the conductive hydrogel adhesive portion of the adhesive being embedded within the continuous sheet portion, the continuous sheet portion being a non-conductive adhesive portion.

17. A device according to claim 10 the conductive hydrogel adhesive portion of the adhesive being embedded within the continuous sheet portion, the continuous sheet portion being a non-conductive adhesive portion, the conductive hydrogel adhesive portion and the continuous sheet portion being disposed in a single layer.

\* \* \* \* \*